United States Patent
Nantermet et al.

(10) Patent No.: US 9,073,879 B2
(45) Date of Patent: Jul. 7, 2015

(54) OXAZOLE DERIVATIVES USEFUL AS MODULATORS OF FAAH

(75) Inventors: Philippe G. Nantermet, Lansdale, PA (US); Zhi-Qiang Yang, Schwenksville, PA (US); Constantine Kreatsoulas, Elkins Park, PA (US); Abbas M. Walji, Lansdale, PA (US); Hong Zhu, Lansdale, PA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 69 days.

(21) Appl. No.: 13/635,286

(22) PCT Filed: Apr. 18, 2011

(86) PCT No.: PCT/US2011/032842
§ 371 (c)(1),
(2), (4) Date: Sep. 14, 2012

(87) PCT Pub. No.: WO2011/133447
PCT Pub. Date: Oct. 27, 2011

(65) Prior Publication Data
US 2013/0012526 A1    Jan. 10, 2013

Related U.S. Application Data

(60) Provisional application No. 61/326,695, filed on Apr. 22, 2010.

(51) Int. Cl.
| | | |
|---|---|---|
| *C07D 413/12* | (2006.01) | |
| *C07D 413/14* | (2006.01) | |
| *C07D 263/46* | (2006.01) | |
| *A61K 31/4545* | (2006.01) | |
| *A61K 31/444* | (2006.01) | |
| *A61K 31/422* | (2006.01) | |
| *C07D 473/32* | (2006.01) | |
| *A61K 31/52* | (2006.01) | |
| *C07D 413/04* | (2006.01) | |
| *A61P 19/02* | (2006.01) | |
| *A61P 29/00* | (2006.01) | |
| *A61P 25/00* | (2006.01) | |
| *A61P 25/06* | (2006.01) | |
| *A61P 25/20* | (2006.01) | |
| *A61P 25/28* | (2006.01) | |
| *A61P 25/16* | (2006.01) | |
| *A61K 31/4439* | (2006.01) | |

(52) U.S. Cl.
CPC ............ *C07D 263/46* (2013.01); *C07D 413/12* (2013.01); *C07D 413/14* (2013.01)

(58) Field of Classification Search
CPC .. C07D 413/12; C07D 413/14; C07D 473/32; C07D 413/04; A61K 31/4545; A61K 31/444; A61K 31/422; A61K 31/52; A61K 31/4439; A61P 19/02; A61P 29/00; A61P 25/00; A61P 25/06; A61P 25/20; A61P 25/28; A61P 25/16
USPC ............ 514/263.22, 340, 318, 338, 333, 339, 514/376; 546/271.4, 194, 256; 548/228; 544/277

See application file for complete search history.

(56) References Cited

FOREIGN PATENT DOCUMENTS

| WO | WO2009154785 A1 | 12/2009 |
|---|---|---|
| WO | WO2010017079 A1 | 2/2010 |

OTHER PUBLICATIONS

STN search transcript with bibliographic data for: Sviripa, V. N.; Prokopenko, V. M.; Brovarets, V. S.; Drach, B. S., Transformations of 2-aryl-4-(dichloromethylene)-5(4H)-oxazolones to arylthio derivatives of substituted oxazoles and 2,5-piperazinediones, Zhurnal Organichnoi to Farmatsevtichnoi Khimii (2004), 2(4), 43-47.*
Pilo, S.G. et al, 2-Aryl-5-arylsulfanyl-1,3-oxazole-4-carboxylic Acids and Their Derivatives, Russian Journal of General Chemistry, 2010, 1345-1350, 80/7, Pleiades Publishing, Ltd.
CAS RN 853409-69-5 STN Entry Date Jun. 30, 2005(5-[(4-Methylphenyl)THIO]-2-Phenyl-4-OXAZOLYL]-4-Morpholinyl-Methanone.
CAS RN 853409-73-1 STN Entry Date Jun. 30, 2005(2-[(4-Methylphenyl)—5[(4-Methylphenyl)THIO]-4-Oxazolyl-4-Morpholinyl-Methanone.

* cited by examiner

*Primary Examiner* — Kendra D Carter
*Assistant Examiner* — Jason A Deck
(74) *Attorney, Agent, or Firm* — Matthew A. Leff; John C. Todaro

(57) ABSTRACT

The present invention is directed to certain Oxazole derivatives which are useful as modulators of Fatty Acid Amide Hydrolase (FAAH) and as FAAH imaging agents. The invention is also concerned with pharmaceutical formulations comprising these compounds as active ingredients and the use of the compounds and their formulations in the treatment of certain disorders, including osteoarthritis, rheumatoid arthritis, diabetic neuropathy, postherpetic neuralgia, skeletomuscular pain, and fibromyalgia, as well as acute pain, migraine, sleep disorder, Alzheimer Disease, and Parkinson's Disease.

7 Claims, No Drawings

SEQUENCE LISTING

```
<160> NUMBER OF SEQ ID NOS: 3

<210> SEQ ID NO 1
<211> LENGTH: 36
<212> TYPE: DNA
<213> ORGANISM: Unknown
<220> FEATURE:
<223> OTHER INFORMATION: Primer

<400> SEQUENCE: 1
caaggtaccg ccaccatggt gctgagcgaa gtgtgg                    36

<210> SEQ ID NO 2
<211> LENGTH: 30
<212> TYPE: DNA
<213> ORGANISM: Unknown
<220> FEATURE:
<223> OTHER INFORMATION: Primer

<400> SEQUENCE: 2
ccggaattct caagatggcc gcttttcagg                           30

<210> SEQ ID NO 3
<211> LENGTH: 30
<212> TYPE: DNA
<213> ORGANISM: Unknown
<220> FEATURE:
<223> OTHER INFORMATION: Primer

<400> SEQUENCE: 3
ccggaattct cacgatggct gcttttgagg                           30
```

OXAZOLE DERIVATIVES USEFUL AS MODULATORS OF FAAH

BACKGROUND OF THE INVENTION

Disclosed herein are compounds that inhibit the activity of fatty acid amide hydrolase (FAAH), compositions that include the compounds, and methods of their use. Compounds disclosed herein as inhibitors of fatty acid amide hydrolase (FAAH) are useful in the treatment of diseases, disorders, or conditions that would benefit from the inhibition of fatty acid amide hydrolase and increases in endogenous fatty acid amides.

Fatty acid amide hydrolase (FAAH) is an enzyme that is abundantly expressed throughout the CNS (Freund et al. Physiol. Rev. 2003; 83:1017-1066) as well as in peripheral tissues, such as, for example, in the pancreas, brain, kidney, skeletal muscle, placenta, and liver (Giang, D. K. et al., Proc. Natl. Acad. Sci. U.S.A. 1997, 94, 2238-2242; Cravatt et al. Proc. Natl. Acad. Sci. U.S.A. 2004, 101, 29, 10821-10826). FAAH hydrolyzes the fatty acid amide (FAA) family of endogenous signaling lipids. General classes of fatty acid amides include the N-acylethanolamides (NAEs) and fatty acid primary amides (FAPAs). Examples of NAEs include anandamide (AEA), palmitoylethanolamide (PEA) and oleoylethanolamide (OEA). An example of FAPAs includes 9-Z-octadecenamide or oleamide. (McKinney M K and Cravatt B F 2005. Annu Rev Biochem 74:411-32). Another class of fatty acid amide family of endogenous signaling lipids is N-acyl taurines that have also been shown to be elevated upon FAAH deletion or inhibition and appear to act on transient receptor potential (TRP) family of calcium channels, although the functional consequences are not yet clear (Saghatelian A, et al. Biochemistry. 2004, 43:14332-9, Saghatelian A, et al. Biochemistry, 2006, 45:9007-9015). In addition to fatty acid amides, FAAH can also hydrolyze certain fatty acid esters, such as, for example, 2-arachidonylglycerol (2-AG) another endocannabinoid (Mechoulam et al. Biochem. Pharmacol. 1995; 50:83-90; Stella et al. Nature, 1997; 388:773-778; Suguria et al. Biochem. Biophys. Res. Commun. 1995, 215:89-97).

Inhibition of FAAH is expected to lead to an increase in the level of anandamide and other fatty acid amides. This increase in fatty acid amides leads to an increase in the noiceptive threshold. Thus, inhibitors of FAAH are useful in the treatment of pain (Cravatt, B F; Lichtman, A H Current Opinion in Chemical Biology 2003, 7, 469-475). Such inhibitors are useful in the treatment of other disorders that can be treated using fatty acid amides or modulators of cannabinoid receptors, such as, for example, anxiety, sleep disorder, Alzheimer disease, and Parkinson's disease, eating disorders, metabolic disorders, cardiovascular disorders, and inflammation (Simon et al Archives of Gen. Psychiatry, 2006, 63, 824-830. Kunos, G et al. *Pharmacol Rev* 2006, 58, 389-462). In some embodiments, FAAH inhibitor compounds may be peripherally restricted and may not substantially affect neural disorders, such as, for example, depression and anxiety. Finally, agonism of cannabinoid receptors has also been shown to reduce the progression of atherosclerosis in animal models (see Steffens et al. Nature, 2005, 434, 782-786; and Steffens et al., Curr. Opin. Lipid., 2006, 17:519-526). Thus, increasing the level of endogenous cannabinergic fatty acid amides (e.g., anandamide) is expected to effectively treat or reduce the risk of developing atherosclerosis.

Inhibition of FAAH also leads to elevation of palmitoylethanolamide which is thought to work, in part, through activation of the peroxisome proliferator-activated receptor α (PPAR-α) to regulate multiple pathways including, for example, pain perception in neuropathic and inflammatory conditions such as convulsions, neurotoxicity, spacticity and to reduce inflammation, for example, in atopic eczema and arthritis (LoVerme J et al. The nuclear receptor peroxisome proliferator-activated receptor-alpha mediates the anti-inflammatory actions of palmitoylethanolamide. *Mol Pharmacol* 2005, 67:15-19; LoVerme J et al. The search for the palmitoylethanolamide receptor. *Life Sci* 2005, 77:1685-1698. Lambert D M et al. The palmitoylethanolamide family: a new class of anti-inflammatory agents? *Curr Med Chem* 2002, 9:663-674; Eberlein B, et al. Adjuvant treatment of atopic eczema: assessment of an emollient containing N-palmitoylethanolamide (ATOPA study). J Eur Acad Dermatol Venereol 2008, 22:73-82. Re G, et al. Palmitoylethanolamide, endocannabinoids and related cannabimimetic compounds in protection against tissue inflammation and pain: potential use in companion animals. Vet J. 2007 173: 21-30.). Thus, inhibition of FAAH is useful for the treatment of various pain and inflammatory conditions, such as osteoarthritis, rheumatoid arthritis, diabetic neuropathy, postherpetic neuralgia, skeletomuscular pain, and fibromyalgia.

It is also thought that certain fatty acid amides, such as, for example, OEA, act through the peroxisome proliferator-activated receptor α (PPAR-α) to regulate diverse physiological processes, including, e.g., feeding and lipolysis. Consistent with this, human adipose tissue has been shown to bind and metabolize endocannabinoids such as anandamide and 2-arachidonylglycerol (see Spoto et al., Biochimie 2006, 88, 1889-1897; and Matias et al., J. Clin. Endocrin. & Met., 2006, 91:3171-3180). Thus, inhibiting FAAH activity in vivo leads to reduced body fat, body weight, caloric intake, and liver triglyceride levels. However, unlike other anti-lipidemic agents that act through PPAR-α, e.g., fibrates, FAAH inhibitors do not cause adverse side effects such as rash, fatigue, headache, erectile dysfunction, and, more rarely, anemia, leukopenia, angioedema, and hepatitis (see, e.g., Muscari et al. Cardiology, 2002, 97:115-121).

Many fatty acid amides are produced on demand and rapidly degraded by FAAH. As a result, hydrolysis by FAAH is considered to be one of the essential steps in the regulation of fatty acid amide levels in the central nervous system as well as in peripheral tissues and fluids. The broad distribution of FAAH combined with the broad array of biological effects of fatty acid amides (both endocannabinoid and non-endocannabinoid mechanisms) suggests that inhibition of FAAH leads to altered levels of fatty acid amides in many tissues and fluids and may be useful to treat many different conditions. FAAH inhibitors increase the levels of endogenous fatty acid amides. FAAH inhibitors block the degradation of endocannabinoids and increase the tissue levels of these endogenous substances. FAAH inhibitors can be used in this respect in the prevention and treatment of pathologies in which endogenous cannabinoids and or any other substrates metabolized by the FAAH enzyme are involved.

The various fatty acid ethanolamides have important and diverse physiological functions. As a result, inhibitor molecules that selectively inhibit FAAH enzymatic activity would allow a corresponding selective modulation of the cellular and extra-cellular concentrations of a FAAH substrate. FAAH inhibitors that are biologically compatible could be effective pharmaceutical compounds when formulated as therapeutic agents for any clinical indication where FAAH enzymatic inhibition is desired. In some embodiments, FAAH activity in peripheral tissues can be preferentially inhibited. In some embodiments, FAAH inhibitors that do substantially cross the blood-brain-barrier can be used to preferentially inhibit FAAH activity in peripheral tissues. In some embodiments, FAAH inhibitors that preferentially inhibit FAAH activity in peripheral tissues can minimize the effects of FAAH inhibition in the central nervous system. In some embodiments, it is preferred to inhibit FAAH activity in peripheral tissues and minimize FAAH inhibition in the central nervous system.

SUMMARY OF THE INVENTION

The present invention is directed to certain Oxazole derivatives which are useful as inhibitors of Fatty Acid Amide Hydrolase (FAAH). The invention is also concerned with pharmaceutical formulations comprising these compounds as active ingredients and the use of the compounds and their formulations in the treatment of certain disorders, including osteoarthritis, rheumatoid arthritis, diabetic neuropathy, postherpetic neuralgia, skeletomuscular pain, and fibromyalgia, as well as acute pain, migraine, sleep disorder, Alzheimer disease, and Parkinson's disease.

DETAILED DESCRIPTION OF THE INVENTION

In one aspect the invention is directed to compounds of formula I:

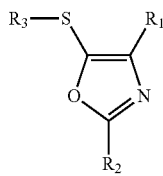

or a pharmaceutically acceptable salt thereof wherein:
$R_1$ is

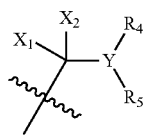

n is 0, 1 or 2;
$X_1$ and $X_2$ are each independently selected from hydrogen, and $C_{1-4}$ alkyl optionally mono, di- or tri-substituted with fluoro, or
$X_1$ and $X_2$ taken together form an oxo group;
Y is selected from O and —N;
$R_4$ is selected from the group consisting of:
  (1) aryl,
  (2) $HET_1$,
  (3) $C_{3-6}$cycloalkyl,
  (4) $CH_2$-aryl,
  (5) $CH_2$—$HET_1$, and
  (6) $CH_2$—$C_{3-6}$cycloalkyl,
wherein $R_4$ is optionally mono or di-substituted with substituents independently selected from the group consisting of:
  (a) halo,
  (b) —CN,
  (c) mono, di or tri-halo alkyl,
  (d) OH,
  (e) mono, di or tri-halo —$OC_{1-4}$ alkyl,
  (f) —$OC_{1-4}$ alkyl, optionally substituted with hydroxyl, halo or amino,
  (g) —$C_{1-4}$alkyl optionally substituted with one or two substituents selected from hydroxyl, CN, —$CHF_2$ and —$CF_3$,
  (h) —$C_{1-2}$alkyl-$C_{3-6}$cycloalkyl optionally substituted with hydroxy, halo or CN,
  (i) —$S(O)_nC_{1-4}$alkyl,
  (j) —$S(O)_nNR^6R^7$,
  (k) —C(O)—NH—$NR^8R^9$,
  (l) —C(O)—OH,
  (m) —C(O)—$OC_{1-4}$alkyl, optionally substituted with halo or hydroxy,
  (n) —C(O)—$NR^{10}R^{11}$,
  (o) —C(O)—$C_{1-4}$alkyl optionally mono, di or tri substituted with halo,
  (p) —$C(NR^{12})$—$NR^{13}R^{14}$,
  (q) $HET^4$,
  (r) aryl,
  (s) —C(O)—NH—NH—C(O)H,
  (t) —$CH_2$—C(O)—O—$C_{1-4}$alkyl, whereas the $CH_2$ may be optionally substituted with $C_{1-4}$alkyl or OH
  (u) —$CH_2$—$C(O)NR^{15}R^{16}$, whereas the $CH_2$ may be optionally substituted with $C_{1-4}$alkyl or OH,
  (v) —$NR^{17}R^{18}$, and
  (w) mono, di or tri-halo $C_{1-4}$alkyl-$NR^{17}R^{18}$,
wherein choices (q) and (r) are each optionally mono or di-substituted with substituents selected from
  (1) halo,
  (2) —CN,
  (3) —OH,
  (4) —$C_{1-4}$alkyl optionally substituted with hydroxy, halo or cyano,
  (5) —$CF_3$,
  (6) —$OC_{1-4}$alkyl optionally substituted with hydroxyl or halo,
  (7) —C(O)OH, and
  (8) —C(O)O—$C_{1-3}$alkyl,
  (9) —C(O)—$NR^{19}R^{20}$,
  (10) $NH_2$,
  (11) oxo, and
  (12) =S,
wherein $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$, are each independently selected from H and $C_{1-4}$alkyl, wherein said $C_{1-4}$alkyl is optionally substituted with $CF_3$,
or
$R^6$ and $R^7$ or $R^8$ and $R^9$ or $R^{10}$ and $R^{11}$ or $R^{13}$ and $R^{14}$ or $R^{15}$ and $R^{16}$ or $R^{17}$ and $R^{18}$ or $R^{19}$ and $R^{20}$ are joined together to form a ring with the atoms to which they are attached there is formed a heterocyclic ring of 4 to 7 atoms, said ring containing 1, 2, 3 or 4 heteroatoms selected from N, O and S, said ring being optionally mono or di-substituted with substituents independently selected from halo, hydroxyl, oxo, $C_{1-4}$alkyl, hydroxy$C_{1-4}$alkyl, halo$C_{1-4}$alkyl, —C(O)—$C_{1-4}$alkyl and —$S(O)nC_{1-4}$alkyl;
$R_5$ is selected from the group consisting of
  (1) hydrogen
  (2) mono, di or tri-halo $C_{1-4}$ alkyl,
  (3) aryl,
  (4) $HET_1$,
  (5) $C_{3-6}$cycloalkyl,
  (6) $CH_2$-aryl,
  (7) $CH_2$—$HET_1$,
  (8) $CH_2$—$C_{3-6}$cycloalkyl,
  (9) —$C_{1-4}$alkyl optionally substituted with one or two substituents selected from hydroxyl, CN, —$CHF_2$ and —$CF_3$, and

(10) —$C_{1-2}$alkyl-$C_{3-6}$cycloalkyl optionally substituted with hydroxy, halo or CN, or $R^4$ and $R^5$ are joined together to form 3-7 membered ring with the atoms to which they are attached, said ring containing 1, 2, 3 or 4 heteroatoms selected from N, O and S, said ring being optionally mono or di-substituted with substituents independently selected from halo, hydroxyl, oxo, $C_{1-4}$alkyl, hydroxy$C_{1-4}$alkyl, halo$C_{1-4}$alkyl, —C(O)—$C_{1-4}$alkyl and —S(O)n$C_{1-4}$alkyl, with the proviso that when Y is O, $R_5$ is not present;

$R^2$ is selected from the group consisting of:
(1) aryl,
(2) $HET^3$, and
(3) —$C_{3-6}$cycloalkyl,
wherein $R^2$ is optionally mono or di-substituted with substituents independently selected from the group consisting of
(a) halo,
(b) —CN,
(c) —OH,
(d) —$NR_{21}R_{22}$, wherein $R_{21}$ and $R_{22}$ are each independently selected from hydrogen and $C_{1-4}$alkyl,
(e) —$C_{1-4}$alkyl optionally substituted with hydroxy, halo or cyano, or amino
(f) —$CF_3$,
(g) —$OC_{1-4}$alkyl optionally substituted with hydroxyl or halo,
(h) —C(O)O—$C_{1-3}$alkyl,
(i) —C(O)$NR_{21}R_{22}$, and
(j) —S-aryl, optionally substituted with halo, $C_{1-4}$alkyl or —$OC_{1-4}$alkyl;

$R_3$ is selected from the group consisting of:
(1) aryl,
(2) $HET^5$, and
(3) —$C_{3-6}$cycloalkyl,
wherein $R_3$ is optionally mono or di-substituted with substituents independently selected from the group consisting of
(a) hydroxy,
(b) halo,
(c) —$C_{3-6}$cycloalkyl,
(d) —$OC_{3-5}$cycloalkyl,
(e) —$C_{1-4}$ alkyl,
(f) —$OC_{1-4}$ alkyl,
(g) —$C(O)CH_3$
(h) mono, di or tri-halo $C_{1-4}$ alkyl,
(i) mono, di or tri-halo —$OC_{1-4}$ alkyl, and
(j) —$S(O)_n$—$C_{1-4}$ alkyl;
wherein aryl is as a mono- or bi-cyclic aromatic ring system; and $HET^1$, $HET^2$, $HET^3$, $HET^4$ and $HET^5$ are each independently a 5 to 10-membered aromatic, partially aromatic or non-aromatic mono- or bicyclic ring, or N-oxide thereof, said containing 1 to 4 heteroatoms selected from O, S and N, and optionally substituted with 1 to 2 oxo groups.

Within this aspect there is a genus wherein:
$R_1$ is

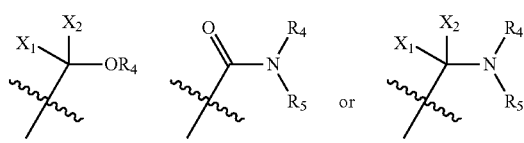

wherein $X_1$ and $X_2$ are each independently selected from hydrogen and methyl.

Within this aspect there is a genus wherein:
$R_4$ is optionally mono- or di-substituted and is selected from the group consisting of:
(1) aryl,
(2) $HET_1$, and
(3) $C_{3-6}$cycloalkyl.
Within this genus there is a sub-genus wherein:
$R_4$ is an optionally mono- or di-substituted:
(1) phenyl,
(2) pyridyl,
(3) pyridazinyl,
(4) pyrimidyl,
(5) pyrazinyl,
(6) thiazolyl,
(7) thienyl,
(8) pyrrolyl,
(9) indolyl,
(10) indazolyl,
(11) benzoxazolyl,
(12) triazolyl,
(13) purinyl, or
(14) cyclohexyl.
Within this sub-genus there is a class wherein:
$R_4$ is an optionally mono- or di-substituted:
(1) phenyl,
(2) pyridyl,
(3) pyridazinyl,
(4) pyrimidyl,
(5) pyrazinyl,
(6) pyrrolyl,
(7) indolyl,
(8) indazolyl, or
(9) cyclohexyl.
Within this aspect there is a genus wherein:
wherein:
$R^4$ is optionally mono or di-substituted with substituents independently selected from the group consisting of:
(a) —CN,
(b) OH,
(c) —$OC_{1-4}$ alkyl, optionally substituted with hydroxyl, halo or amino,
(d) —$C_{1-4}$alkyl optionally substituted with one or two substituents selected from hydroxyl, CN, —$CHF_2$ and —$CF_3$,
(e) —$S(O)_nC_{1-4}$alkyl,
(f) —$S(O)_nNR^6R^7$,
(g) —C(O)—NH—$NR^8R^9$,
(h) —C(O)—OH,
(i) —C(O)—$OC_{1-4}$alkyl, optionally substituted with halo or hydroxy,
(k) —C(O)—$NR^{10}R^{11}$,
(l) $HET^4$,
(m) aryl, and
(n) —$NR^{17}R^{18}$,
wherein choices (l) and (m) are each optionally mono or di-substituted with substituents selected from
(1) halo,
(2) —CN,
(3) —OH,
(4) —$C_{1-4}$alkyl optionally substituted with hydroxy, halo or cyano,
(5) —$CF_3$,
(6) —$OC_{1-4}$alkyl optionally substituted with hydroxyl or halo,
(7) —C(O)OH, and
(8) —C(O)O—$C_{1-3}$alkyl,
(9) —C(O)—$NR^{19}R^{20}$,
(10) —$NH_2$,

(11) oxo, and
(12) =S.
Within this genus there is a sub-genus wherein:
R$^4$ is optionally mono or di-substituted with substituents independently selected from the group consisting of
(a) OH,
(b) —C$_{1-4}$alkyl optionally substituted with one or two substituents selected from hydroxyl, CN, —CHF$_2$ and —CF$_3$,
(c) —C(O)—OC$_{1-4}$alkyl, optionally substituted with halo or hydroxy,
(d) —C(O)—NR$^{10}$R$^{11}$,
(e) HET$^4$,
(f) aryl, and
(g) —NR$^{17}$R$^{18}$,
wherein choices (e) and (f) are each optionally mono or di-substituted with substituents selected from
(1) halo,
(2) —CN,
(3) —OH,
(4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH, and
(8) —C(O)O—C$_{1-3}$ alkyl;
(9) —C(O)—NR$^{19}$R$^{20}$,
(10) —NH$_2$, and
(11) oxo.
Within this sub-genus there is a class wherein:
R$^4$ is optionally mono or di-substituted with substituents independently selected from the group consisting of:
(a) OH,
(b) —C(O)—OC$_{1-4}$alkyl, optionally substituted with halo or hydroxy,
(c) —C(O)—NR$^{10}$R$^{11}$,
(d) HET$^4$, and
(e) —NR$^{17}$R$^{18}$,
wherein choice (d) is optionally mono or di-substituted with substituents selected from
(1) —CN,
(2) —OH, and
(3) —NH$_2$.
Within this aspect there is a genus wherein:
R$_5$ is selected from the group consisting of:
(1) hydrogen,
(2) HET$_1$,
(3) C$_{3-6}$cycloalkyl, and
(4) —C$_{1-4}$alkyl optionally substituted with one or two substituents selected from hydroxyl, CN, —CHF$_2$ and —CF$_3$.
Within this genus there is a sub-genus wherein:
R$_5$ is selected from the group consisting of:
(1) hydrogen, and
(2) mono, di or tri-halo C$_{1-4}$ alkyl.
Within this aspect there is a genus wherein:
R$^2$ is selected from the group consisting of:
(1) phenyl,
(2) cyclopropyl,
(3) cyclohexyl,
(4) pyridinyl, and
(5) tetrahydropyranyl,
wherein R$^2$ is optionally mono or di-substituted with substituents independently selected from the group consisting of
(a) —OH,
(b) —NH$_2$,
(c) —C$_{1-4}$alkyl optionally substituted with hydroxy, halo or cyano, or amino, and
(d) —C(O)O—C$_{1-3}$alkyl.

Within this aspect there is a genus wherein:
R$_3$ is selected from the group consisting of:
(1) phenyl,
(2) pyridyl,
(3) pyridazinyl,
(4) pyrimidyl,
(5) pyrazinyl,
(6) pyrrolyl, and
(7) cyclohexyl,
wherein R$_3$ is optionally mono or di-substituted with substituents independently selected from the group consisting of
(a) halo,
(b) —C$_{1-4}$ alkyl, and
(c) —S(O)$_n$—C$_{1-4}$ alkyl.
Within this genus there is a sub-genus wherein:
R$_3$ is selected from the group consisting of:
(1) phenyl, and
(2) pyridyl,
wherein R$_3$ is optionally mono or di-substituted with halo.
Within this aspect there is a genus wherein:
R$_1$ is

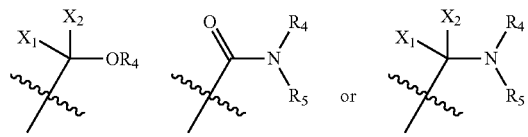

wherein X$_1$ and X$_2$ are each independently selected from hydrogen and methyl;
R$_4$ is an optionally mono- or di-substituted:
(1) phenyl,
(2) pyridyl,
(3) pyridazinyl,
(4) pyrimidyl,
(5) pyrazinyl,
(6) thiazolyl,
(7) thienyl,
(8) pyrrolyl,
(9) indolyl,
(10) indazolyl,
(11) benzoxazolyl,
(12) triazolyl,
(13) purinyl, or
(14) cyclohexyl;
wherein R$^4$ is optionally mono or di-substituted with substituents independently selected from the group consisting of:
(a) OH,
(b) —C$_{1-4}$alkyl optionally substituted with one or two substituents selected from hydroxyl, CN, —CHF$_2$ and —CF$_3$,
(c) —C(O)—OC$_{1-4}$alkyl, optionally substituted with halo or hydroxy,
(d) —C(O)—NR$^{10}$R$^{11}$,
(e) HET$^4$,
(f) aryl, and
(g) —NR$^{17}$R$^{18}$,
wherein choices (e) and (f) are each optionally mono or di-substituted with substituents selected from
(1) halo,
(2) —CN,
(3) —OH,
(4) —C$_{1-4}$alkyl optionally substituted with hydroxy, halo or cyano, (5) —CF$_3$,
(6) —OC$_{1-4}$alkyl optionally substituted with hydroxyl or halo,
(7) —C(O)OH, and
(8) —C(O)O—C$_{1-3}$alkyl,
(9) —C(O)—NR$^{19}$R$^{20}$,
(10) —NH$_2$, and
(11) oxo;
R$_5$ is selected from the group consisting of:
(1) hydrogen,
(2) HET$_1$,
(3) C$_{3-6}$cycloalkyl, and
(4) —C$_{1-4}$alkyl optionally substituted with one or two substituents selected from hydroxyl, CN, —CHF$_2$ and —CF$_3$;
R$^2$ is selected from the group consisting of:
(1) phenyl,
(2) cyclopropyl,
(3) cyclohexyl,
(4) pyridinyl, and
(5) tetrahydropyranyl,
wherein R$^2$ is optionally mono or di-substituted with substituents independently selected from the group consisting of
(a) —OH,
(b) —NH$_2$,
(c) —C$_{1-4}$alkyl optionally substituted with hydroxy, halo or cyano, or amino, and
(d) —C(O)O—C$_{1-3}$alkyl;
R$_3$ is selected from the group consisting of:
(1) phenyl,
(2) pyridyl,
(3) pyridazinyl,
(4) pyrimidyl,
(5) pyrazinyl,
(6) pyrrolyl, and
(7) cyclohexyl,
wherein R$_3$ is optionally mono or di-substituted with substituents independently selected from the group consisting of
(a) halo,
(b) —C$_{1-4}$ alkyl, and
(c) —S(O)$_n$—C$_{1-4}$ alkyl.
Within this genus there is a sub-genus wherein:
R$_1$ is

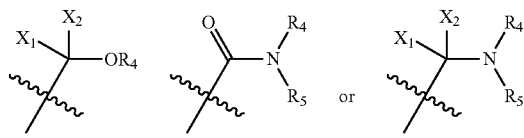

wherein X$_1$ and X$_2$ are each independently selected from hydrogen and methyl;
R$_4$ is an optionally mono- or di-substituted:
(1) phenyl,
(2) pyridyl,
(3) pyridazinyl,
(4) pyrimidyl,
(5) pyrazinyl,
(6) pyrrolyl,
(7) indolyl,
(8) indazolyl, or
(9) cyclohexyl;
R$^4$ is optionally mono or di-substituted with substituents independently selected from the group consisting of:

(a) OH,
(b) —C(O)—OC$_{1-4}$alkyl, optionally substituted with halo or hydroxy,
(c) —C(O)—NR$^{10}$R$^{11}$,
(d) HET$^4$,
(e) —NR$^{17}$R$^{18}$,
wherein choice (d) is optionally mono or di-substituted with substituents selected from
(1) —CN,
(2) —OH, and
(3) —NH$_2$;
R$_5$ is selected from the group consisting of:
(1) hydrogen, and
(2) mono, di or tri-halo C$_{1-4}$ alkyl;
R$^2$ is selected from the group consisting of:
(1) phenyl,
(2) cyclopropyl,
(3) cyclohexyl,
(4) pyridinyl, and
(5) tetrahydropyranyl,
wherein R$^2$ is optionally mono or di-substituted with substituents independently selected from the group consisting of
(a) —OH,
(b) —NH$_2$,
(c) —C$_{1-4}$alkyl optionally substituted with hydroxy, halo or cyano, or amino, and
(d) —C(O)O—C$_{1-3}$alkyl.
R$_3$ is selected from the group consisting of:
(1) phenyl, and
(2) pyridyl,
wherein R$_3$ is optionally mono or di-substituted with halo.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature.

Examples of isotopes suitable for inclusion in the compounds of the invention include isotopes of hydrogen such as 2H and 3H, carbon such as $^{11}C$, $^{13}C$ and $^{14}C$, nitrogen such as 13N and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{23}I$ and $^{125}I$, and chlorine such as $^{36}Cl$.

Certain isotopically-labelled compounds of Formula I, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes propynyl, 1-methylethynyl, butynyl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aryloxy" means an aryl group as defined above attached to a molecule by an oxygen atom (aryl-0) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by a sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

The term "HET", such as in "HET$^1$", "HET$^2$", "HET$^3$", "HET$^4$" is defined as a 5- to 10-membered aromatic, partially aromatic or non-aromatic mono- or bicyclic ring, containing 1-4 heteroatoms selected from O, S and N, and optionally substituted with 1-2 oxo groups. Where applicable, the Het group shall be defined to include the N-oxide. Preferably, "HET" is a 5- or 6-membered aromatic or non-aromatic monocyclic ring containing 1-3 heteroatoms selected from O, S and N, for example, pyridine, pyrimidine, pyridazine, furan, thiophene, thiazole, oxazole, isooxazole and the like, or HET is a 9- or 10-membered aromatic or partially aromatic bicyclic ring containing 1-3 heteroatoms selected from O, S, and N, for example, benzofuran, benzothiophene, indole, pyranopyrrole, benzopyran, quionoline, benzocyclohexyl, napthyridine and the like. "HET" also includes the following: benzimidazolyl, benzofuranyl, benzopyrazolyl, benzotriazolyl, benzothiophenyl, benzoxazolyl, carbazolyl, carbolinyl, cinnolinyl, (uranyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl. In one aspect "HET" is selected from pyridyl, pyridazinyl, pyrimidinyl, pyrazinyl, thiazolyl, thienyl, pyrrolyl, oxazolyl, and oxadiazole;

For all of the above definitions, each reference to a group is independent of all other references to the same group when referred to in the Specification. For example, if both $R^1$ and $R^2$ are HET, the definitions of HET are independent of each other and $R^1$ and $R^2$ may be different HET groups, for example furan and thiophene.

The ability of the compounds of Formula I to selectively inhibit FAAH makes them useful for treating, preventing or reversing the progression of a variety of inflammatory and non-inflammatory diseases and conditions.

Diseases, disorders, syndromes and/or conditions, that would benefit from inhibition of FAAH enzymatic activity include, for example, Alzheimer's Disease, schizophrenia, depression, alcoholism, addiction, suicide, Parkinson's disease, Huntington's disease, stroke, emesis, miscarriage, embryo implantation, endotoxic shock, liver cirrhosis, atherosclerosis, cancer, traumatic head injury, glaucoma, and bone cement implantation syndrome.

Other diseases, disorders, syndromes and/or conditions that would benefit from inhibition of FAAH activity, include, for example, multiple sclerosis, retinitis, amyotrophic lateral sclerosis, immunodeficiency virus-induced encephalitis, attention-deficit hyperactivity disorder, pain, nociceptive pain, neuropathic pain, inflammatory pain, noninflammatory pain, painful hemorrhagic cystitis, obesity, hyperlipidemia, metabolic disorders, feeding and fasting, alteration of appetite, stress, memory, aging, hypertension, septic shock, cardiogenic shock, intestinal inflammation and motility, irritable bowel syndrome, colitis, diarrhea, ileitis, ischemia, cerebral ischemia, hepatic ischemia, myocardial infarction, cerebral excitotoxicity, seizures, febrile seizures, neurotoxicity, neuropathies, sleep, induction of sleep, prolongation of sleep, insomnia, and inflammatory diseases. Neurological and psychological disorders that would benefit from inhibition of FAAH activity include, for example, pain, depression, anxiety, generalized anxiety disorder (GAD), obsessive compulsive disorders, stress, stress urinary incontinence, attention deficit hyperactivity disorders, schizophrenia, psychosis, Parkinson's disease, muscle spasticity, epilepsy, diskenesia, seizure disorders, jet lag, and insomnia.

FAAH inhibitors can also be used in the treatment of a variety of metabolic syndromes, diseases, disorders and/or conditions, including but not limited to, insulin resistance syndrome, diabetes, hyperlipidemia, fatty liver disease, obesity, atherosclerosis and arteriosclerosis. FAAH inhibitors are useful in the treatment of a variety of painful syndromes, diseases, disorders and/or conditions, including but not limited to those characterized by non-inflammatory pain, inflammatory pain, peripheral neuropathic pain, central pain, differentiation pain, chronic nociceptive pain, stimulus of nociceptive receptors, phantom and transient acute pain.

Inhibition of FAAH activity can also be used in the treatment of a variety of conditions involving inflammation. These conditions include, but are not limited to arthritis (such as rheumatoid arthritis, shoulder tendonitis or bursitis, gouty arthritis, and aolymyalgia rheumatica), organ-specific inflammatory diseases (such as thyroiditis, hepatitis, inflammatory bowel diseases), asthma, other autoimmune diseases (such as multiple sclerosis), chronic obstructive pulmonary disease (COPD), allergic rhinitis, and cardiovascular diseases.

In some cases, FAAH inhibitors are useful in preventing neurodegeneration or for neuroprotection.

In addition, it has been shown that when FAAH activity is reduced or absent, one of its substrates, anandamide, acts as a substrate for COX-2, which converts anandamide to prostamides (Weber et al J Lipid. Res. 2004; 45:757). Concentrations of certain prostamides may be elevated in the presence of a FAAH inhibitor. Certain prostamides are associated with reduced intraocular pressure and ocular hypotensivity. Thus, in one embodiment, FAAH inhibitors may be useful for treating glaucoma.

In some embodiments, FAAH inhibitors can be used to treat or reduce the risk of EMDs, which include, but are not limited to, obesity, appetite disorders, overweight, cellulite, Type I and Type II diabetes, hyperglycemia, dyslipidemia, steatohepatitis, liver steatosis, non-alcoholic steatohepatitis, Syndrome X, insulin resistance, diabetic dyslipidemia, anorexia, bulimia, anorexia nervosa, hyperlipidemia, hypertriglyceridemia, atherosclerosis, arteriosclerosis, inflammatory disorders or conditions, Alzheimer's disease, Crohn's disease, vascular inflammation, inflammatory bowel disorders, rheumatoid arthritis, asthma, thrombosis, or cachexia.

In other embodiments, FAAH inhibitors can be used to treat or reduce the risk of insulin resistance syndrome and diabetes, i.e., both primary essential diabetes such as Type I Diabetes or Type II Diabetes and secondary nonessential diabetes. Administering a composition containing a therapeutically effective amount of an in vivo FAAH inhibitor reduces the severity of a symptom of diabetes or the risk of developing a symptom of diabetes, such as atherosclerosis, hypertension, hyperlipidemia, liver steatosis, nephropathy, neuropathy, retinopathy, foot ulceration, or cataracts.

In another embodiment, FAAH inhibitors can be used to treat food abuse behaviors, especially those liable to cause excess weight, e.g., bulimia, appetite for sugars or fats, and non-insulin-dependent diabetes.

In some embodiments, FAAH inhibitors can be used to treat a subject suffering from an EMD and also suffers from a depressive disorder or from an anxiety disorder. Preferably, the subject is diagnosed as suffering from the depressive or psychiatric disorder prior to administration of the FAAH inhibitor composition. Thus, a dose of a FAAH inhibitor that is therapeutically effective for both the EMD and the depressive or anxiety disorder is administered to the subject.

Preferably, the subject to be treated is human. However, the methods can also be used to treat non-human mammals. Animal models of EMDs, such as those described in e.g., U.S. Pat. No. 6,946,491, are particularly useful.

FAAH inhibitor compositions can also be used to decrease body-weight in individuals wishing to decrease their body weight for cosmetic, but not necessarily medical considerations.

A FAAH inhibitor composition can be administered in combination with a drug for lowering circulating cholesterol levels (e.g., statins, niacin, fibric acid derivatives, or bile acid binding resins). FAAH inhibitor compositions can also be used in combination with a weight loss drug, e.g., orlistat or an appetite suppressant such as diethylpropion, mazindole, orlistat, phendimetrazine, phentermine, or sibutramine.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The following abbreviations have the indicated meanings:
AIBN=2.2'-azobisisobutyronitrile
B.P.=benzoyl peroxide
Bn=benzyl
$CCl_4$=carbon tetrachloride
D=—O$(CH_2)_3$O—
DAST=diethylamine sulfur trifluoride
DCC=dicyclohexyl carbodiimide
DCI=1-(3-dimethylaminopropyl)-3-ethyl carbodiimide
DEAD=diethyl azodicarboxylate
DIBAL=diisobutyl aluminum hydride
DME=ethylene glycol dimethylether
DMAP=4-(dimethylamino)pyridine
DMF=N,N-dimethylformamide
DMSO=dimethyl sulfoxide
$Et_3N$=triethylamine
LDA=lithium diisopropylamide
m-CPBA=metachloroperbenzoic acid
NBS=N-bromosuccinimide
NSAID=non-steroidal anti-inflammatory drug
PCC=pyridinium chlorochromate
PDC=pyridinium dichromate
Ph=phenyl
1,2-Ph=1,2-benzenediyl
Pyr=pyridinediyl
Qn=7-chloroquinolin-2-yl
$R^S$=—$CH_2SCH_2CH_2$Ph
r.t.=room temperature
rac.=racemic
THF=tetrahydrofuran
THP=tetrahydropyran-2-yl Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof; and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

For the treatment of FAAH mediated diseases the compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative, and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Assays

The following assays illustrate the utility of the invention:

The compounds of the invention underwent pharmacological evaluations to determine their inhibitory effect on the enzyme FAAH (Fatty Acid Amide Hydrolase).

To assist in assay development stable cell lines for human, murine and rat full length FAAH were developed. Human FAAH cDNA (Accession No: NM_001441.1) was purchased from Origene (Rockville, Md.). The full length FAAH was subcloned into the mammalian expression vector, pcDEF.neo, using XbaI and EcoRI restriction sites and used for stable cell line generation.

| Construct | | Primer Sequence |
|---|---|---|
| Full length rodent FAAH | 1 | CAAGGTACCGCCACCATGGTGCTGAGCGAAGTGTGG |
| Full length murine FAAH | 2 | CCGGAATTCTCAAGATGGCCGCTTTTCAGG |
| Full length rat FAAH | 3 | CCGGAATTCTCACGATGGCTGCTTTTGAGG |

Murine (accession number NM_010173) and Rat FAAH (accession number NM_024132) was amplified by reverse transcriptase polymerase chain reaction (RT-PCR) from brain cDNA (BD Biosciences, San Jose, Calif.) using primers 1 and 2 or primers 1 and 3 respectively (see Table). The resulting PCR product was ligated into pCR4 TOPO and DNA sequence confirmed. The full length murine FAAH was subcloned into the mammalian expression vector, pcDEFneo using either EcoRI (murine) or KpnI and EcoRI (rat) restriction sites. Chinese hamster ovary cells (CHO) were transfected following manufacturers protocol (AMAXA). Forty eight hours post transfection, cells were trypsinized and transferred to 96 well plates in Iscove's DMEM media supplemented with 2 mM Glutamine, 10% fetal calf serum, 1 mg/ml geneticin and HT Supplement (0.1 mM sodium hypoxanthine, 0.016 mM thymidine) in order to isolate single clones. Following selection in geneticin, individual clones were selected and FAAH activity was assessed using a whole cell fluorescent anandamide assay, modified from Ramarao et al (2005). Following removal of tissue culture media cells were dislodged following addition of Cellstripper (Mediatech, Inc. Manassas, Va.) and transferred to 96 well black clear bottom assay plate, centrifuged at 1,000 rpm for 3 mins and media removed and replaced with assay buffer (50 mM Tris pH 8.0, 1 mM EDTA, 0.1% fatty acid free BSA). The reaction was initiated by addition of fluorescent substrate, AMC Arachidonoyl Amide (Cayman Chemical, Ann Arbor, Mich.) to 1 µM and reaction allowed to proceed for 2 hours at room temperature. Release of fluorescence was monitored in a CytoFluor Multiplate Reader. Cells expressing the highest amount of FAAH activity were selected for study with FAAH inhibitors.

Preparation of Lysate and Microsomes

CHO cells expressing FAAH were used to prepare either crude cell lysate or microsome fractions. To harvest cells, tissue culture media was decanted, the monolayer washed three times with $Ca^{++}Mg^{++}$ free PBS and cells recovered after 15 mm in enzyme free dissociation media (Millipore Corp, Billerica, Mass.). Cells were collected by centrifuging at 2000 rpm for 15 min. and the cell pellet re-suspended with 50 mM HEPES (pH 7.4) containing 1 mM EDTA and the protease inhibitors aprotinin (1 mg/ml) and leupeptin (100 µM). The suspension was sonicated at 4° C. and the cell lysate recovered after centrifuging at 12,000×g (14,600 rpm, SS34 rotor) for 20 min at 4° C. to form a crude pellet of cell debris, nuclei, peroxisomes, lysosomes, and mitochondria; the supernatant or cell lysate was used for FAAH enzyme assay. In some cases, microsomes fractions enriched in FAAH were prepared by centrifuging the cell lysate further at 27,000 rpm (100,000×g) in SW28 rotor for 50 minutes at 4° C. The pellet containing FAAH-enriched microsomes was re-suspend in 50 mM HEPES, (pH 7.4) 1 mM EDTA, and any remaining DNA sheared by passage of material through a 23 gauge needle and aliquots of enzyme were store at −80° C. prior to use.

FAAH Assays

Several assays have been used to demonstrate the inhibitory activity. Enzyme activity was demonstrated in a radioenzymatic test based on measuring the product of hydrolysis (ethanolamine [$^3$H]) of anandamide [ethanolamine 1-.sup.3H] (American Radiolabeled Chemicals; 1 mCi/ml) with FAAH (Life Sciences (1995), 56, 1999-2005 and Journal of Pharmacology and Experimented Therapeutics (1997), 283, 729-734), Analytical. Biochemistry (2003), 318:270-5. In addition, routine assays were performed monitoring hydrolysis of araehidonyl-7-amino-4-methylcoumarin amide (AAMCA) by following increase in fluorescence upon release of 7-amino 4-methyl coumarin ($\lambda_{EX}$=355 nm, $\lambda_{EM}$=460 nm). Analytical. Biochemistry (2005). 343:143-51

Assays are performed on either cell lysate or microsome fractions prepared as described or in whole cell format employing either the fluorescent substrate AAMCA (Cayman chemical, Ann Arbor, Mich.) or $^3$H-anandamide ([ETHANOLAMINE-1-3H] American Radiolabeled Chemicals; 1 mCi/ml). The cell lysate or microsome assay is performed in black PerkinElmer OptiPlates-384F by adding FAAH_CHO (whole cell (shown as human Whole cell or Human WC), cell lysate (shown as human lysate of human LY) or microsome) in assay buffer (50 mM Phosphate, pH 8.0, 1 mM EDTA, 200 mM KCl, 0.2% glycerol, 0.1% fatty acid free BSA) to each well, followed by either DMSO or compound and allowed to incubate at 22-25° C. for fifteen minutes. AAMCA substrate was used to achieve a final concentration of 1 µM and reaction allowed to proceed at room temperature for 1-3 hours. Fluorescent release as a measure of FAAH activity was monitored by reading the plate in an Envision plate Reader (Ex: 360/40 nM; Em: 460/40 nM). Whole cell assay is conducted with cells harvested after rinsing tissue culture flasks three times with $Ca^{++}Mg^{++}$ free PBS, incubating for 10 min in Enzyme free dissociation media and centrifuging for 5 minutes at 1,000 rpm in table top centrifuge. Cells are resuspended in assay buffer at desired cell number in ($4 \times 10^4$ cells/assay in 96-well format; $1 \times 10^4$ cells/assay in 384-well format) and assayed as described.

Alternatively, assays are performed using anandamide [ethanolamine 1-.sup.3H] (specific activity of 10 Ci/mmol) diluted with cold anandamide to achieve a final assay concentration of 1 µM anandamide (~50,000 cpm). Enzyme (CHO cell lysate, brain or liver homogenate) is incubated in assay buffer (50 mM Phosphate, pH 8.0, 1 mM EDTA, 200 mM KCl, 0.2% glycerol, 0.1% fatty acid free BSA) with inhibitor at 25° C. for 30 minutes. The reaction was terminated by addition of 2 volumes of chloroform:methanol (1:1) and mixed by vortexing. Following a centrifugation step, 2000 rpm for 10 min. at room temperature, the aqueous phase containing the released $^3$H-ethanolamide was recovered and quantitated by liquid scintillation as a reflection of FAAH enzyme activity.

Ramarao M. K., et al. A fluorescence-based assay for fatty acid amide hydrolase compatible with high-throughput screening. Anal. Biochem. 343:143-51 (2005)

Wilson S. J., et 1. A high-throughput-compatible assay for determining the activity of fatty acid amide hydrolase. Anal Biochem. 318:270-5 (2003).

Each of the Examples was tested and found to demonstrate biological activity. Results for specific Examples are provided below. Each of Examples was found to have and IC50 of 10 μM or lower in these assays.

Biological Results table

| Example No. | human cell_IC50 (nM) | human lysate_IC50 (nM) |
|---|---|---|
| A5.1 | 388 | 61 |
| A5.2 | 400 | 57 |
| A5.3 | 39 | 10 |
| B2.3 | 535 | 54 |
| B2.11 | 13 | 2 |
| B2.11.3 | 1454 | 149 |
| B2.2 | 507 | 55 |
| B5.1 | 18 | 3 |
| B5.2 | 461 | 56 |
| B2.4 | 224 | 24 |
| B2.5 | 143 | 20 |
| B2.6 | 360 | 47 |
| B2.7 | 201 | 12 |
| B2.11.2 | 14 | 3 |
| B2.9 | 10 | 2 |
| B7.1 | 39 | 8 |
| B7.2 | 80 | 21 |
| B2.1 | 20 | 3 |
| B2.10 | 298 | 56 |
| B2.11.4 | 5 | 3 |
| B2.8 | 513 | 130 |
| B2.11.1 | 253 | 59 |
| B2.11.5 | 22 | 5 |
| B2.12 | 2153 | 807 |
| B5.2 | 17 | 4 |
| B2.15 | 343 | 88 |
| B2.14 | 3364 | 902 |
| B5.4 | 8 | 3 |
| B2.16 | 10 | 4 |
| B5.6 | 38 | 22 |
| B5.7 | 24 | 6 |
| B5.9 | 139 | 45 |
| B5.10 | 31 | 12 |
| B5.8 | 42 | 17 |
| B5.11 | 50 |  |
| D4.1 | 1308 | 187 |
| D4.2 | 979 | 317 |
| B5.13 | 2826 |  |
| B2.17 | 97 |  |
| B5.14 | 27 |  |

Preparation of the Compounds of the Invention.

The compounds of the present invention can be prepared according to the procedures denoted in the following reaction Schemes and Examples or modifications thereof using readily available starting materials, reagents, and conventional procedures thereof well-known to a practitioner of ordinary skill in the art of synthetic organic chemistry. Specific definitions of variables in the Schemes are given for illustrative purposes only and are not intended to limit the procedures described.

General Scheme

Scheme A depicts the synthesis of oxazole-esters of type A3. Carbonylation of triflates A1 (see WO2010/017079A1) under Pd⁰ catalysis affords esters A3 that can be hydrolysed and converted to the corresponding amides A5 under standard peptide coupling conditions.

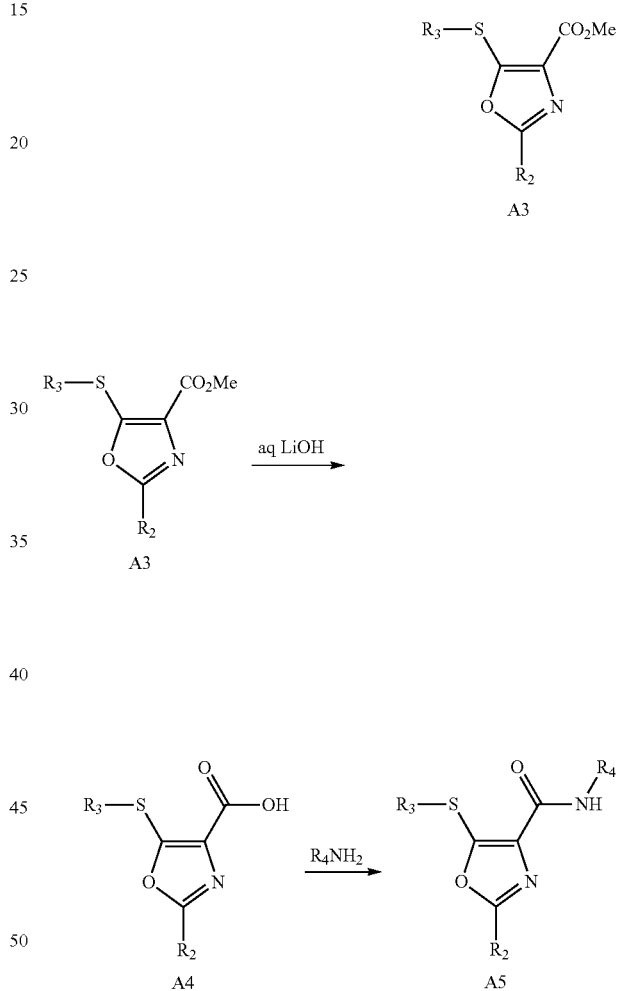

Scheme B depicts the ethers of type B2. Reduction of methyl esters A3 provides alcohols B1 which can be converted to the corresponding ethers B2 from alcohols $R_4OH$, under Mistunobu conditions, or from the corresponding bromides $R_4Br$. Alternatively, alcohols B1 can be converted to bromides B3 which serve as precursors to ethers B2 (alkylation of alcohols $R_4OH$) or aminomethyl derivatives of type B5 via amines $R_4R_5NH$. Aldehydes of type B4, available from the oxidation of alcohols B1 can also be converted to aminomethyl derivatives of type B5 via reductive amination with amines $R_4R_5NH$. Addition of Grignard reagents RMgBr to aldehydes B4 can lead to the preparation of substituted alcohols of type B6 which can afford ethers B7.

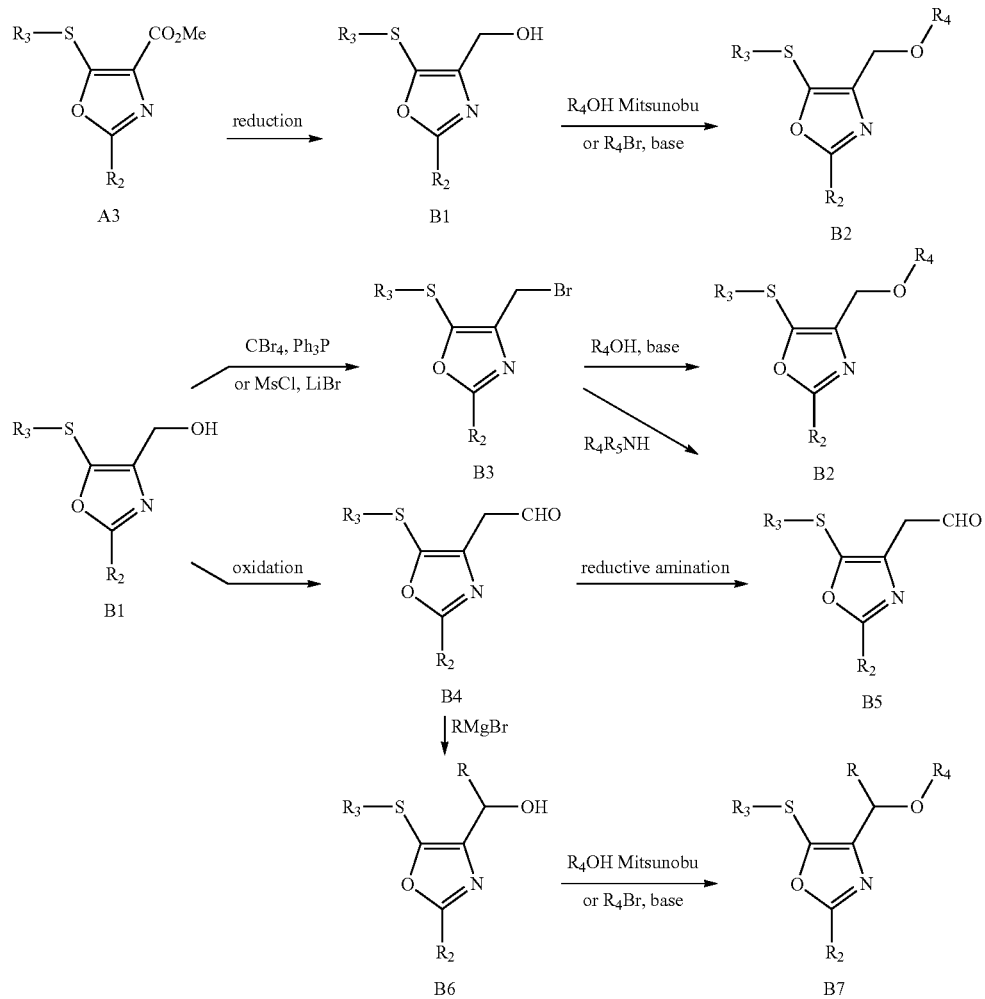
Scheme C describes the preparation of thiooxazoles of type C3 from carboxylic acids $R_2CO_2H$ and aminothioether C1 using a similar procedure as described by Magnus et al. (*Tetrahedron Lett.* 2002, 34, 7393). Bromination with NBS, lithium-halogen exchange followed by trapping with DMF affords aldehydes of type C5.
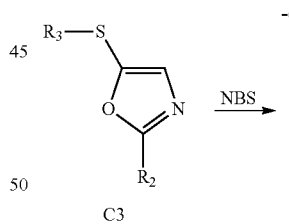
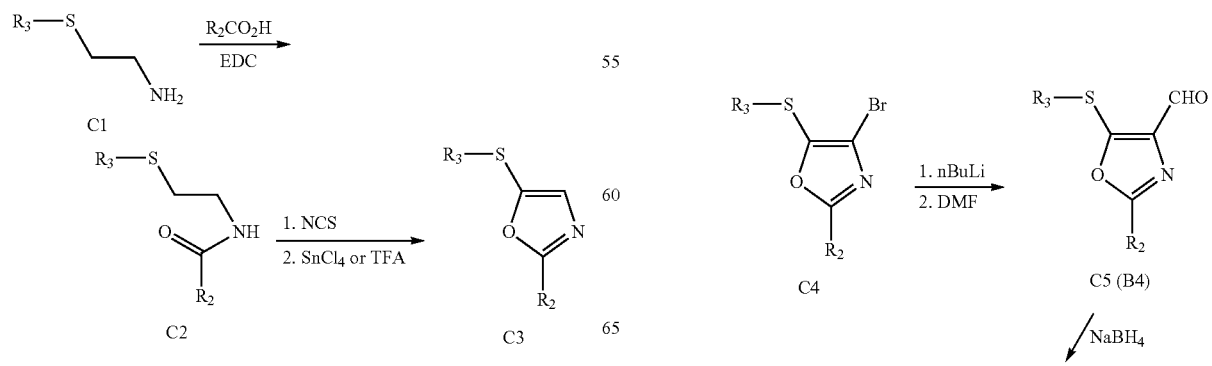

-continued

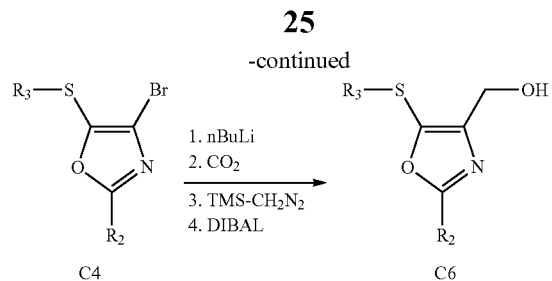

Scheme D describes an alternative preparation of hydrometrhyloxazoles of type D4. Imidates of type D1 (available from methanolysis of the corresponding nitriles) can be reacted with serine methyl ester to provide oxazolines of type D2. Oxidation to the corresponding oxazoles, bromination and reduction affords bromo-hydroxymethyl-oxazoles of type D3. Mitsunobu reaction with alcohols R$_4$OH, followed by alkylation of with thiols R$_3$SH provides ethers of type D4.

Scheme D

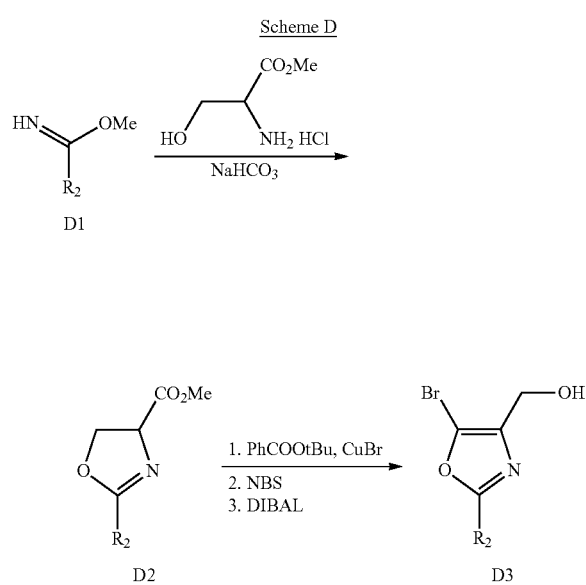

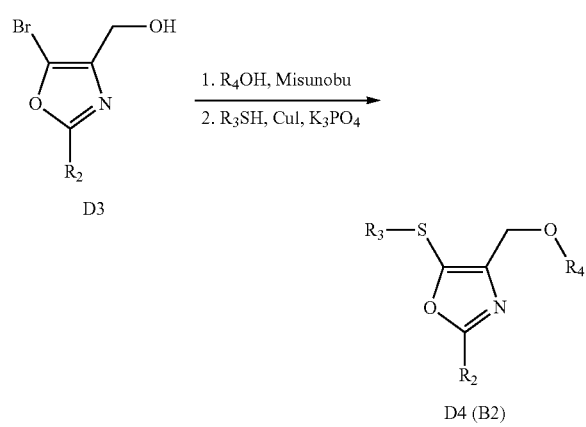

Intermediate A4.1

5-[(5-chloropyridin-2-yl)sulfanyl]-2-(4-fluorophenyl)-1,3-oxazole-4-carboxylic acid

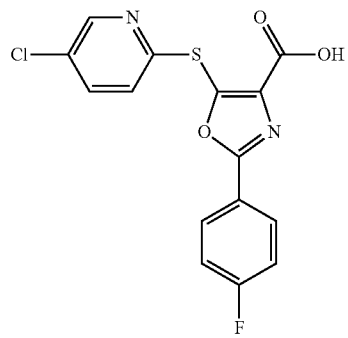 [SMILES: O=C(O)c1nc(-c2ccc(F)cc2)oc1Sc1ccc(Cl)cn1]

To a solution of 2-(4-fluorophenyl)-1,3-oxazol-4-yl trifluoromethanesulfonate (30 g, 96 mmol, WO2010/017079A1) in DMF (200 ml) was added methanol (78 ml, 1928 mmol) followed by palladium (II) acetate (2.164 g, 9.64 mmol) and dppp (3.98 g, 9.64 mmol). Triethylamine (26.9 ml, 193 mmol) was added and the reaction mixture was purged with CO for 3 minutes, placed under balloon pressure of CO, stirred at 65° C. for 2 h, allowed to cool to room temperature and poured onto ice water. The reaction mixture was extracted with DCM, dried over Na$_2$SO$_4$, filtered, concentrated and purified by flash chromatography (silica, 10-50% EtOAc/heptanes) to provide methyl 2-(4-fluorophenyl)-1,3-oxazole-4-carboxylate (7.4 g).

To a solution of 2-(4-fluorophenyl)-1,3-oxazole-4-carboxylate (6.15 g, 27.8 mmol) in CCl$_4$ (155 mL) was added bromine (0.716 ml, 13.90 mmol) and the reaction mixture was stirred at RT for 3 days, concentrated in vacuo and purified by flash chromatography (silica, 15-45% EtOAc/heptanes) to provide methyl 5-bromo-2-(4-fluorophenyl)-1,3-oxazole-4-carboxylate (3.38 g). LCMS [M+Na]=322.

To a solution of 5-bromo-2-(4-fluorophenyl)-1,3-oxazole-4-carboxylate (3.38 g, 11.26 mmol) in NMP (100 mL) was added potassium carbonate (4.67 g, 33.8 mmol) and 5-chloropyridine-2-thiol (1.8 g, 12.39 mmol) and the reaction mixture was stirred at 70° C. for 16 h, allowed to cool to RT and diluted with water (340 mL). The precipitated solid was filtered and purified by flash chromatography (silica, 10-50% EtOAc/heptanes) to provide 5-[(5-chloropyridin-2-yl)sulfanyl]-2-(4-fluorophenyl)-1,3-oxazole-4-carboxylate (2.7 g). LCMS [M+Na]=387.

To a solution of methyl 5-[(5-chloropyridin-2-yl)sulfanyl]-2-(4-fluorophenyl)-1,3-oxazole-4-carboxylate (0.20 g, 0.55 mmol) in 6 ml of 1:1 MeOH/THF was added 1N LiOH (2.19 ml, 2.19 mmol). After 1 h at room temperature, the reaction was acidified by 3N HCl. The reaction mixture was diluted with water and extracted with EtOAc. The combined organics were washed with brine, dried over Na$_2$SO$_4$, filtered and concentrated to yield 5-[(5-chloropyridin-2-yl)sulfanyl]-2-(4-fluorophenyl)-1,3-oxazole-4-carboxylic acid as a white solid (0.19 g). The acid was used without further purification. LCMS [M+H]=351.3. $^1$H NMR (400 MHz, CDCl$_3$) δ 8.39 (d, J=3 Hz, 1H), 8.09 (dd, J=8.6, 5.5 Hz, 2H), 7.61 (dd, J=8.5, 3 Hz, 1H), 7.24 (d, J=8.6 Hz, 1H), 7.15 (dd, J=8.6, 8.6 Hz, 2H), 3.94 (s, 3H).

Intermediate B1.1

{5-[(5-chloropyridin-2-yl)sulfanyl]-2-(4-fluorophenyl)-1,3-oxazol-4-yl}methanol

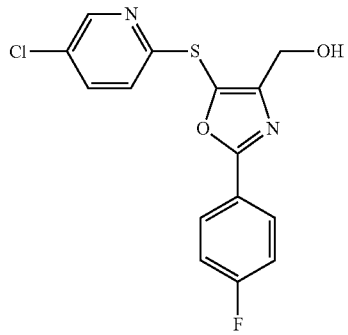 [SMILES: OCc1nc(-c2ccc(F)cc2)oc1Sc1ccc(Cl)cn1]

To a solution of methyl 5-[(5-chloropyridin-2-yl)sulfanyl]-2-(4-fluorophenyl)-1,3-oxazole-4-carboxylate (0.15 g, 0.41 mmol) in 1 ml of THF at −78° C. was added 1M DIBAL-H in toluene (1.03 ml, 1.03 mmol) dropwise. After 5 min, the reaction was allowed to warm to room temperature and stirred for 4 h. Water (0.1 ml), 10% NaOH (0.1 ml) and celite were added to the reaction solution and the mixture was filtered. Washed with THF and the filtrate was dried over Na$_2$SO$_4$, filtered, concentrated and purified by flash chromatography (silica, 20-50% EtOAc/hexanes) to provide {5-[(5-chloropyridin-2-yl)sulfanyl]-2-(4-fluorophenyl)-1,3-oxazol-4-yl}methanol as white solid: $^1$H NMR (400 MHz, CDCl$_3$) δ 8.37 (d, J=2.5 Hz, 1H), 8.05 (m, 2H), 7.56 (dd, J=8.4, 2.5 Hz, 1H), 7.13 (m, 3H), 4.72 (d, J=6.2 Hz, 2H), 2.98 (d, J=6.2 Hz, 1H); LCMS [M+H]$^+$=337.3.

Intermediate B3.1

2-{[4-(bromomethyl)-2-(4-fluorophenyl)-1,3-oxazol-5-yl]sulfanyl}-5-chloropyridine

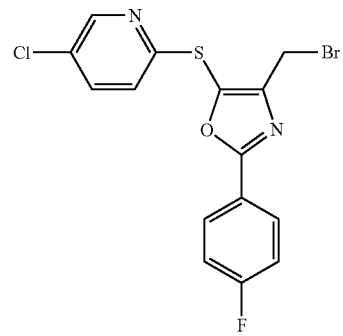 [SMILES: Fc1ccc(-c2nc(CBr)c(Sc3ccc(Cl)cn3)o2)cc1]

To a solution of {5-[(5-chloropyridin-2-yl)sulfanyl]-2-(4-fluorophenyl)-1,3-oxazol-4-yl}methanol (intermediate B1.1, 0.30 g, 0.89 mmol) in 3.3 mL of DCM at 0° C. was added imidazole (0.02 g, 0.36 mmol), Ph$_3$P (0.28 g, 1.07 mmol) and CBr$_4$ (0.36 g, 1.07 mmol). After 1 h at 0° C., water was added and the reaction mixture was extracted with EtOAc. The combined organics were washed with 10% KHSO$_4$, satd. NaHCO$_3$ and brine, dried over Na$_2$SO$_4$, filtered and concentrated. The reaction was purified by flash chromatography (silica, 0-25% EtOAc/hexanes) to give 2-{[4-(bromomethyl)-2-(4-fluorophenyl)-1,3-oxazol-5-yl]sulfanyl}-5-chloropyridine as white solid. LCMS [M+H]$^+$=401.2.

Intermediate B4.1

5-[(5-chloropyridin-2-yl)sulfanyl]-2-(4-fluorophenyl)-1,3-oxazole-4-carbaldehyde

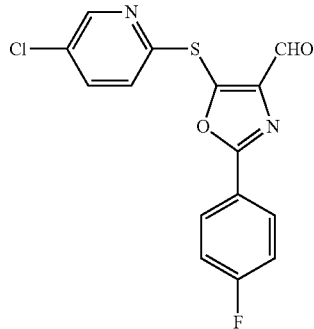 [SMILES: O=Cc1nc(-c2ccc(F)cc2)oc1Sc1ccc(Cl)cn1]

To a solution of {5-[(5-chloropyridin-2-yl)sulfanyl]-2-(4-fluorophenyl)-1,3-oxazol-4-yl}methanol (intermediate B1.1, 0.10 g, 0.30 mmol) in 5.5 ml of DCM was added pyridine (0.24 ml, 2.97 mmol), followed by Dess-Martin periodinane (0.166 g, 0.39 mmol). The reaction was allowed to proceed at rt for 2 h and quenched by the adding of 1M aq. sodium thiosulfate (5 ml) and satd. NaHCO3 (5 ml). After stirring vigorously, the reaction was diluted with water and extracted with EtOAc. The combined organics were washed with brine, dried over Na$_2$SO$_4$ and concentrated to yield 105 mg of 5-[(5-chloropyridin-2-yl)sulfanyl]-2-(4-fluorophenyl)-1,3-oxazole-4-carbaldehyde. The aldehyde was used without further purification. LCMS [M+H]$^+$=335.3.

Intermediate B6.1

1-{5-[(5-chloropyridin-2-yl)sulfanyl]-2-(4-fluorophenyl)-1,3-oxazol-4-yl}ethanol

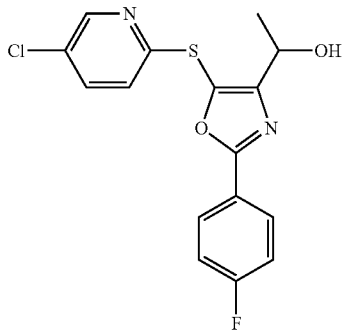 [SMILES: CC(O)c1nc(-c2ccc(F)cc2)oc1Sc1ccc(Cl)cn1]

To a solution of 5-[(5-chloropyridin-2-yl)sulfanyl]-2-(4-fluorophenyl)-1,3-oxazole-4-carbaldehyde (intermediate B4.1, 0.05 g, 0.15 mmol) in THF (1.3 ml) was added 3M methylmagnesium bromide (0.06 ml, 0.18 mmol) at 0° C. The reaction was allowed to warm to rt and satd. aq. NH₄Cl was added. Extracted with EtOAc. The combined organics were washed with brine, dried over Na₂SO₄, concentrated and purified by flash chromatography (silica, 20-50% EtOAc/hexanes) to give 1-{5-[(5-chloropyridin-2-yl)sulfanyl]-2-(4-fluorophenyl)-1,3-oxazol-4-yl}ethanol. $^1$H NMR (400 MHz, CDCl₃) δ 8.36 (d, 2.5 Hz, 1H), 8.06 (m, 2H), 7.52 (dd, J=8.4, 2.5 Hz, 1H), 7.12 (m, 3H), 5.02 (m, 1H), 3.22 (d, J=5.2 Hz, 1H), 1.56 (m, 3H); LCMS [M+H]⁺=351.3.

Intermediate C5.1

5-[(4-chlorophenyl)sulfanyl]-2-(tetrahydro-2H-pyran-4-yl)-1,3-oxazole-4-carbaldehyde

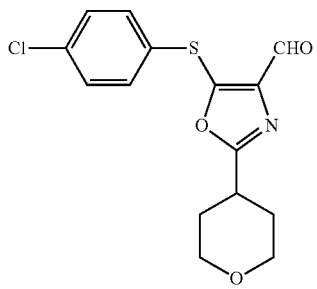 [SMILES: O=Cc1nc(C2CCOCC2)oc1Sc1ccc(Cl)cc1]

Step C5.1-1: N-{2-[(4-chlorophenyl)sulfanyl]ethyl}tetrahydro-2H-pyran-4-carboxamide

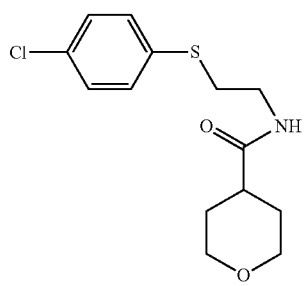 [SMILES: O=C(NCCSc1ccc(Cl)cc1)C1CCOCC1]

To a solution of 2-[(4-chlorophenyl)sulfanyl]ethanamine (15.32 g, 82 mmol, prepared from 4-chlorothiophenol and 2-chloroethylamine) in DMF (247 ml) was added sequentially tetrahydro-2H-pyran-4-carboxylic acid (9.66 g, 74.2 mmol), EDC (15.65 g, 82 mmol) and HOAt (2.021 g, 14.85 mmol) and the reaction mixture was stirred at RT overnight. The reaction mixture was diluted with EtOAc, washed with 1N HCl, aq NaHCO₃, 3M LiCl, dried over sodium sulfate, concentrated in vacuo and purified by flash chromatography (silica 1 kg, 50 to 100% EtOAc in hexane), to give N-{2-[(4-chlorophenyl)sulfanyl]ethyl}tetrahydro-2H-pyran-4-carboxamide (18.25 g). MS: M+H=300. H¹NMR (400 MHz, CDCl₃) δ: 7.31 (d, J=9.9 Hz, 2H), 7.26 (d, J=9.9 Hz, 2H), 5.82 (br s, 1H), 4.40-3.96 (m, 2H), 3.46 (dt, J=7 Hz, 7 Hz, 2H), 3.45-3.36 (m, 2H), 3.05 (t, J=7 Hz, 2H), 2.34-2.26 (m, 1H), 1.82-1.65 (m, 4H).

Step C5.1-2: 5-[(4-chlorophenyl)sulfanyl]-2-(tetrahydro-2H-pyran-4-yl)-1,3-oxazole

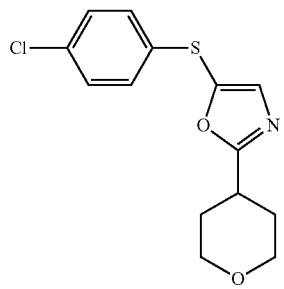 [SMILES: Clc1ccc(Sc2cnc(C3CCOCC3)o2)cc1]

To a solution of N-{2-[(4-chlorophenyl)sulfanyl]ethyl}tetrahydro-2H-pyran-4-carboxamide (9.48 g, 31.6 mmol) in chlorobenzene (316 ml) was added NCS (8.44 g, 63.2 mmol) by portions and the reaction mixture was stirred at RT for 1 h. TFA (1.218 ml, 15.81 mmol) was added and the reaction mixture was stirred at RT for 16 h. The reaction mixture was diluted with DCM, washed with aq NaHCO₃, dried over sodium sulfate, concentrated in vacuo and purified by flash chromatography (silica 2×330 g, 0 to 50% EtOAc in hexane), to give 5-[(4-chlorophenyl)sulfanyl]-2-(tetrahydro-2H-pyran-4-yl)-1,3-oxazole (7.45 g) as a white solid. MS: M+H=296. H¹NMR (400 MHz, CDCl₃) δ: 7.27 (d, 0.1=10.3 Hz, 2H), 7.26 (s, 1H), 7.17 (d, J=10.3 Hz, 2H), 4.01 (dt, J=12.2 Hz, 3.7 Hz, 2H), 3.51 (td, J=12.2 Hz, 3.7 Hz, 2H), 3.10-3.00 (m, 1H), 2.04-1.85 (m, 4H).

Step C5.1-3: 4-bromo-5-[(4-chlorophenyl)sulfanyl]-2-(tetrahydro-2H-pyran-4-yl)-1,3-oxazole

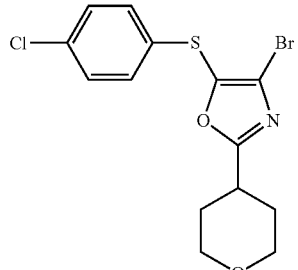

To a solution of 5-[(4-chlorophenyl)sulfanyl]-2-(tetrahydro-2H-pyran-4-yl)-1,3-oxazole (5.21 g, 17.61 mmol) in DCM (176 ml) was added NBS (3.45 g, 19.38 mmol) and the reaction mixture was stirred at RT for 16 h. The reaction mixture was concentrated in vacuo and purified by flash chromatography (silica 330 g, 5 to 30% EtOAc in hexane), to give 4-bromo-5-[(4-chlorophenyl)sulfanyl]-2-(tetrahydro-2H-pyran-4-yl)-1,3-oxazole (6.16 g). MS: M+H=376. H¹NMR (400 MHz, CDCl₃) δ: 7.28 (d, J=8.4 Hz, 2H), 7.22 (d, J=8.4

Hz, 2H), 4.01 (dt, J=11.7 Hz, 3.6 Hz, 2H), 3.50 (td, J=11.7 Hz, 2.7 Hz, 2H), 3.09-2.98 (m, 1H), 2.02-1.86 (m, 4H).

Step C5.1-4: 5-[(4-chlorophenyl)sulfanyl]-2-(tetrahydro-2H-pyran-4-yl)-1,3-oxazole-4-carbaldehyde

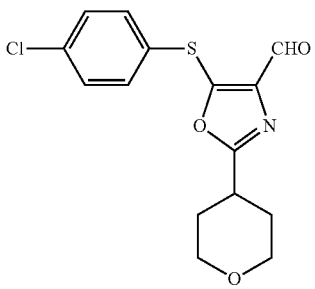 [SMILES: O=Cc1nc(C2CCOCC2)oc1Sc1ccc(Cl)cc1]

To a dry flask was added 4-bromo-5-[(4-chlorophenyl)sulfanyl]-2-(tetrahydro-2H-pyran-4-yl)-1,3-oxazole (810 mg, 2.162 mmol) and THF (21.6 mL), and the reaction mixture was cooled to 78° C. nBuLi (1.486 mL, 2.378 mmol) was added slowly and the reaction mixture was stirred at −78° C. for 5 min. DMF (0.837 mL, 10.81 mmol) was added and the reaction mixture was stirred at −78° C. for 10 min, quenched with water, allowed to warm to RT. The reaction mixture was extracted with EtOAc, washed with 3M LiCl, dried over sodium sulfate and concentrated in vacuo to give 5-[(4-chlorophenyl)sulfanyl]-2-(tetrahydro-2H-pyran-4-yl)-1,3-oxazole-4-carbaldehyde (830 mg crude) to be used as is in the next step. MS: M+H=324.

Intermediate C6.1

{5-[(4-chlorophenyl)sulfanyl]-2-(tetrahydro-2H-pyran-4-yl)-1,3-oxazol-4-yl}methanol

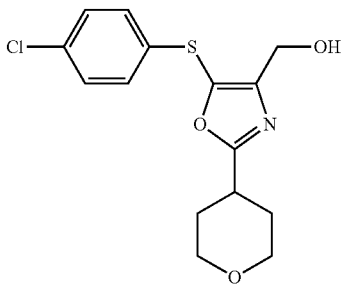 [SMILES: OCc1nc(C2CCOCC2)oc1Sc1ccc(Cl)cc1]

To a dry flask was added 4-bromo-5-[(4-chlorophenyl)sulfanyl]-2-(tetrahydro-2H-pyran-4-yl)-1,3-oxazole (50 mg, 0.133 mmol) and THF (2669 µl), and the reaction mixture was cooled to −78° C. nBuLi (92 µl, 0.147 mmol) was added slowly and the reaction mixture was stirred at −78° C. for 30 min. Crushed dry ice was added, the reaction mixture was stirred at −78° C. for 20 min, quenched with 10% KHSO$_4$, and allowed to warm to RT. The reaction mixture was extracted with EtOAc, dried over sodium sulfate and concentrated in vacuo to give 5-[(4-chlorophenyl)sulfanyl]-2-(tetrahydro-2H-pyran-4-yl)-1,3-oxazole-4-carboxylic acid (47 mg crude) to be used as is in the next step. MS: M+H=340.

To a solution of 5-[(4-chlorophenyl)sulfanyl]-2-(tetrahydro-2H-pyran-4-yl)-1,3-oxazole-4-carboxylic acid (45 mg, 0.132 mmol) in MeOH (2649 µl) was added TMS-diazomethane (132 µl, 0.265 mmol, 2M in Et$_2$O). Additional TMS-diazomethane aliquots were added until no more gas evolution was observed. The reaction mixture was concentrated in vacuo and purified by flash chromatography (silica 12 g, 0 to 50% EtOAc in hexane), to give methyl 5-[(4-chlorophenyl)sulfanyl]-2-(tetrahydro-2H-pyran-4-yl)-1,3-oxazole-4-carboxylate (30 mg). methyl 5-[(4-chlorophenyl)sulfanyl]-2-(tetrahydro-2H-pyran-4-yl)-1,3-oxazole-4-carboxylate was reduced using DIBAL, using a similar procedure as described in the preparation of {5-[(5-chloropyridin-2-yl)sulfanyl]-2-(4-fluorophenyl)-1,3-oxazol-4-yl}methanol (INTERMEDIATE B1.1), to provide {5-[(4-chlorophenyl)sulfanyl]-2-(tetrahydro-2H-pyran-4-yl)-1,3-oxazol-4-yl}methanol. MS: M+H=326.

Intermediate D3.1

(5-bromo-2-cyclopropyl-1,3-oxazol-4-yl)methanol

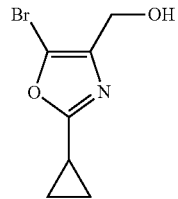

Step D3.1-1: methyl 2-cyclopropyl-4,5-dihydro-1,3-oxazole-4-carboxylate

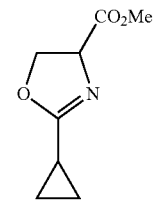 [SMILES: COC(=O)C1COC(C2CC2)=N1]

HCl gas was bubbled slowly into a solution of cyclopropanecarbonitrile (268 g, 4.00 mol, 1.00 equiv.) in methanol (140.8 g, 4.40 mol, 1.10 equiv.) and ether (2500 mL) at 0° C. over 5 hours. The resulting solution was stirred for 24 hours at 0° C. The solid was collected by filtration, washed with 1×500 mL of ether and 1×500 mL of hexane, dried in an oven under reduced pressure. This resulted in 427 g (78% yield) of methyl cyclopropanecarbimidate hydrochloride as a white solid.

Into a 500-mL 3-necked round-bottom flask were placed methyl cyclopropanecarbimidate hydrochloride (13.6 g, 100.00 mmol, 1.00 equiv.), methyl 2-amino-3-hydroxypropanoate hydrochloride (17.6 g, 112.82 mmol, 1.10 equiv.) and dichloromethane (150 mL). The resulting solution was stirred for 24 hours at room temperature, then added sodium bicarbonate (16.8 g, 200.00 mmol, 2.00 equiv.). The resulting solution was stirred for 24 hours at room temperature. The solid was filtered out. The filtrate was concentrated under vacuum. The residue was applied onto a silica gel column and eluted with ethyl acetate/petroleum ether (1:2). This resulted in 8 g (47% yield) of methyl 2-cyclopropyl-4,5-dihydrooxazole-4-carboxylate as a colorless oil.

Step D3.1-2:
(5-bromo-2-cyclopropyl-1,3-oxazol-4-yl)methanol

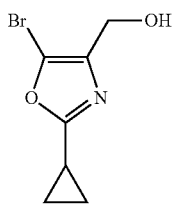 [SMILES: OCc1nc(C2CC2)oc1Br]

Into a 10000-mL 3-necked round-bottom flask were placed methyl 2-cyclopropyl-4,5-dihydrooxazole-4-carboxylate (294 g, 1.74 mol, 1.00 equiv.), CuBr (274 g, 1.92 mol, 1.10 equiv.) and toluene (3000 mL). This was followed by the addition of tert-butyl perbenzoate (506 g, 2.61 mol, 1.50 equiv.) dropwise with stirring at 60° C. over 60 minutes. The resulting solution was stirred overnight at 80° C. in an oil bath. The reaction mixture was cooled to room temperature, then quenched by the addition of 2000 mL of 10% NH$_4$OH. The resulting solution was extracted with 3×2000 mL of ethyl acetate. The organic layers were combined, dried over anhydrous sodium sulfate and concentrated under vacuum. The residue was applied onto a silica gel column and eluted with ethyl acetate/petroleum ether (1:20). This resulted in 200 g (69% yield) of methyl 2-cyclopropyloxazole-4-carboxylate as a yellow oil.

Into a 5000-mL 3-necked round-bottom flask were placed methyl 2-cyclopropyloxazole-4-carboxylate (140 g, 838.32 mmol, 1.00 equiv.), NBS (224 g, 1.26 mol, 1.50 equiv.), CCl$_4$ (1400 mL) and BPO (20 g, 82.64 mmol, 0.10 equiv). The resulting solution was stirred overnight at room temperature, then it was diluted with 2000 mL of EtOAc. The solid was filtrated out. The filtrate was dried over anhydrous calcium chloride and concentrated under vacuum. The residue was applied onto a silica gel column and eluted with ethyl acetate/petroleum ether (1:50~1:20). This resulted in 120 g (58% yield) of methyl 5-bromo-2-cyclopropyloxazole-4-carboxylate as a white solid.

Into a 5000-mL 3-necked round-bottom flask purged and maintained with an inert atmosphere of nitrogen was placed a solution of methyl 5-bromo-2-cyclopropyloxazole-4-carboxylate (120 g, 487.80 mmol, 1.00 equiv.) in tetrahydrofuran (1200 mL). This was followed by the addition of DIBAL-H (1200 mL, 4.00 equiv., 25%) dropwise with stirring at −78° C. over 15 minutes. The resulting solution was stirred for 2 hours at −78~−10° C., then quenched by the addition of 2000 mL of 2N HCl. The resulting solution was extracted with 3×3000 mL of ethyl acetate. The organic layers were combined, dried over anhydrous sodium sulfate and concentrated under vacuum. The crude product was re-crystallized from EAOAc:PE in the ratio of 1:20. This resulted in 70 g (66% yield) of ethyl 5-bromo-2-cyclopropyloxazole-4-carboxylate as a white solid. LC-MS (ES, m/z): 218 [M+H]$^+$.

H$^1$NMR (400 MHz, CDCl$_3$) δ: 4.459 (2H, s), 2.011~2.065 (1H, m), 1.628 (1H, br), 1.020~1.106 (4H, m).

Example A5.1

5-[(5-chloropyridin-2-yl)sulfanyl]-2-(4-fluorophenyl)-N-[4-(methylsulfonyl)phenyl]-1,3-oxazole-4-carboxamide

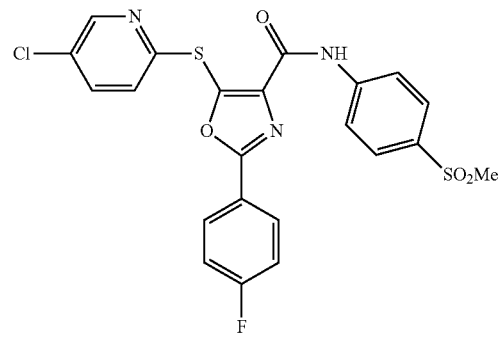 [SMILES: CS(=O)(=O)c1ccc(NC(=O)c2nc(-c3ccc(F)cc3)oc2Sc2ccc(Cl)cn2)cc1]

To a solution of 5-[(5-chloropyridin-2-yl)sulfanyl]-2-(4-fluorophenyl)-1,3-oxazole-4-carboxylic acid (intermediate A 4.1, 15 mg, 0.043 mmol), 4-(methylsulfonyl)aniline (7.32 mg, 0.043 mmol) and DIPEA (0.015 ml, 0.086 mmol) in 0.6 mL of DMF was added BOP (22.7 mg, 0.051 mmol). The reaction was stirred at room temperature for 1 h and purified by reverse phase HPLC to give 5-[(5-chloropyridin-2-yl)sulfanyl]-2-(4-fluorophenyl)-N-[4-(methylsulfonyl)phenyl]-1,3-oxazole-4-carboxamide: $^1$H NMR (400 MHz, CDCl$_3$) δ 9.30 (s, 1H), 8.38 (d, J=2.5 Hz, 1H), 8.08 (m, 2H), 7.94 (s, 4H), 7.61 (dd, J=8.4, 2.5 Hz, 1H), 7.31 (d, J=8.4 Hz, 1H), 7.19 (m, 2H), 3.06 (s, 3H); HRMS exact mass calc for C22H15ClFN3O4S2 [M+H]$^+$: 504.0245; observed: 504.0249.

Examples in Table A5.1-4 are prepared from 5-[(5-chloropyridin-2-yl)sulfanyl]-2-(4-fluorophenyl)-1,3-oxazole-4-carboxylic acid (INTERMEDIATE A4.1) and the appropriate amine, using a procedure similar as described in the preparation of 5-[(5-chloropyridin-2-yl)sulfanyl]-2-(4-fluorophenyl)-N-[4-(methylsulfonyl)phenyl]-1,3-oxazole-4-carboxamide (EXAMPLE A5.1).

TABLE A5.1-4

| Ex # | Structure | Name | M + 1 |
|---|---|---|---|
| A5.1 | 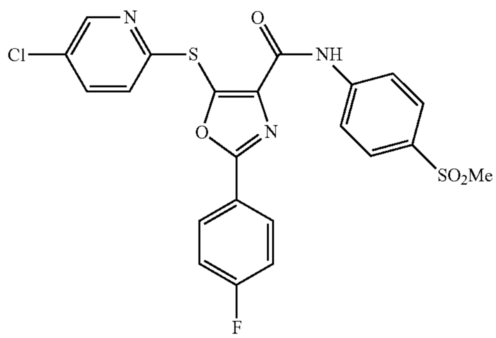 [SMILES: CS(=O)(=O)c1ccc(NC(=O)c2nc(-c3ccc(F)cc3)oc2Sc2ccc(Cl)cn2)cc1] | 5-[(5-chloropyridin-2-yl)sulfanyl]-2-(4-fluorophenyl)-N-[4-(methylsulfonyl)phenyl]-1,3-oxazole-4-carboxamide | 504 |
| A5.2 | 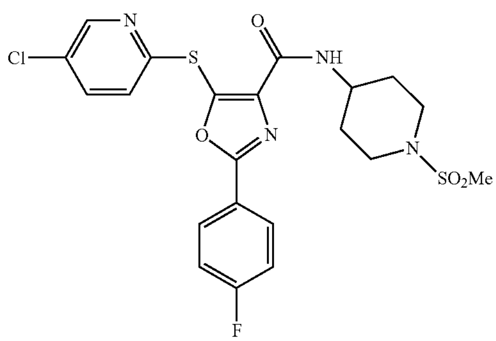 [SMILES: CS(=O)(=O)N1CCC(NC(=O)c2nc(-c3ccc(F)cc3)oc2Sc2ccc(Cl)cn2)CC1] | 5-[(5-chloropyridin-2-yl)sulfanyl]-2-(4-fluorophenyl)-N-[1-(methylsulfonyl)piperidin-4-yl]-1,3-oxazole-4-carboxamide | 511 |
| A5.3 | 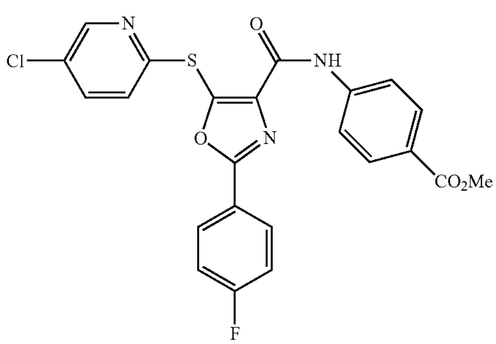 [SMILES: COC(=O)c1ccc(NC(=O)c2nc(-c3ccc(F)cc3)oc2Sc2ccc(Cl)cn2)cc1] | methyl 4-[({5-[(5-chloropyridin-2-yl)sulfanyl]-2-(4-fluorophenyl)-1,3-oxazol-4-yl}carbonyl)amino]benzoate | 484 |
| A5.4 | 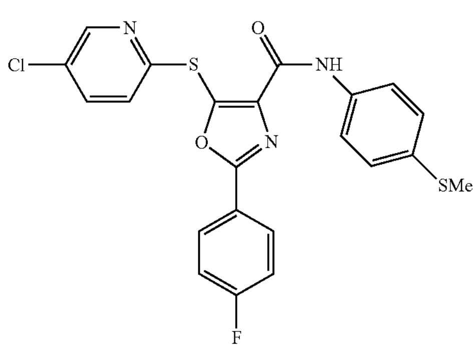 [SMILES: CSc1ccc(NC(=O)c2nc(-c3ccc(F)cc3)oc2Sc2ccc(Cl)cn2)cc1] | 5-chloro-2-{[2-(4-fluorophenyl)-4-{[4-(methylsulfanyl)phenoxy]methyl}-1,3-oxazol-5-yl]sulfanyl}pyridine | 459 |

Example B2.1

5-[(5-[(5-chloropyridin-2-yl)sulfanyl]-2-(4-fluorophenyl)-1,3-oxazol-4-yl]methoxy)-1H-indazole

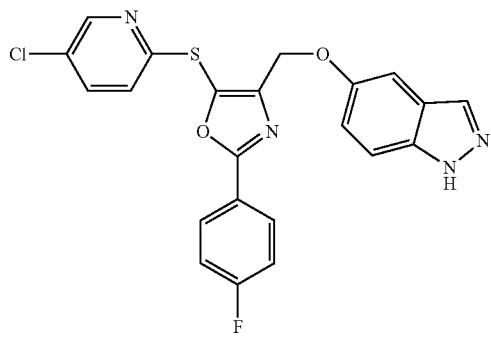 [SMILES: Fc1ccc(-c2nc(COc3ccc4[nH]ncc4c3)c(Sc3ccc(Cl)cn3)o2)cc1]

To a solution of {5-[(5-chloropyridin-2-yl)sulfanyl]-2-(4-fluorophenyl)-1,3-oxazol-4-yl}methanol (intermediate B1.1, 0.12 g, 0.36 mmol) in THF (3 ml) was added 1H-indazole-5-ol (0.1 g, 0.71 mmol), Ph₃P (0.19 g, 0.71 mmol) and DIAD (0.14 ml, 0.71 mmol). The reaction was stirred at rt for 3 h, concentrated and purified by flash chromatography (silica, 30-60% EtOAc/hexanes) to give 5-({5-[(5-chloropyridin-2-yl)sulfanyl]-2-(4-fluorophenyl)-1,3-oxazol-4-yl}methoxy)-1H-indazole as white solid. $^1$H NMR (400 MHz, CDCl$_3$) δ 9.95 (s, 1H), 8.32 (d, J=2.5 Hz, 1H), 8.10 (m, 2H), 7.89 (s, 1H), 7.32 (m, 2H), 7.23 (d, J=2.2 Hz, 1H), 7.15 (t, J=8.6 Hz, 2H), 7.09 (m, 1H), 5.17 (s, 2H); HRMS exact mass talc for C22H14ClFN4O2S [M+H]$^+$: 453.0583; observed: 453.0584.

Examples in Table B2.1-10 are prepared from {5-[(5-chloropyridin-2-yl)sulfanyl]-2-(4-fluorophenyl)-1,3-oxazol-4-yl}methanol (INTERMEDIATE B1.1) and the appropriate alcohol, using a procedure similar as described in the preparation of 5-({5-[(5-chloropyridin-2-yl)sulfanyl]-2-(4-fluorophenyl)-1,3-oxazol-4-yl}methoxy)-1H-indazole (EXAMPLE B2.1).

TABLE B2.1-10

| Ex # | Structure | Name | comments | M + 1 |
|---|---|---|---|---|
| B2.1 | 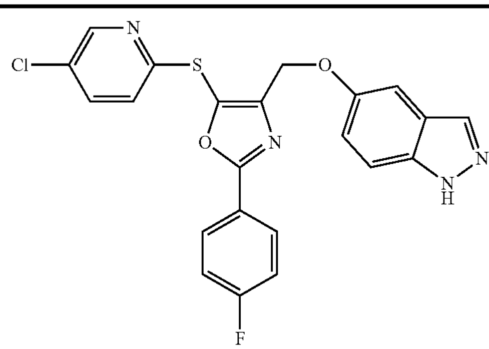 | 5-({5-[(5-chloropyridin-2-yl)sulfanyl]-2-(4-fluorophenyl)-1,3-oxazol-4-yl}methoxy)-1H-indazole | | 453 |
| B2.2 | 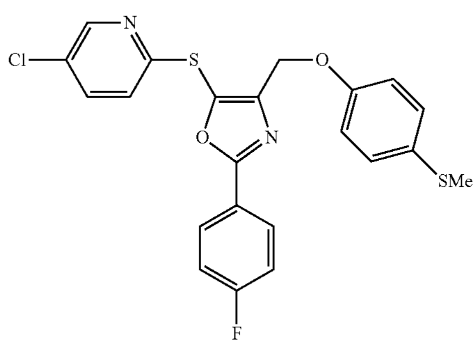 [SMILES: CSc1ccc(OCc2nc(-c3ccc(F)cc3)oc2Sc2ccc(Cl)cn2)cc1] | 5-chloro-2-{[2-(4-fluorophenyl)-4-{[4-(methylsulfanyl)phenoxy]methyl}-1,3-oxazol-5-yl]sulfanyl}pyridine | | 459 |
| B2.3 | 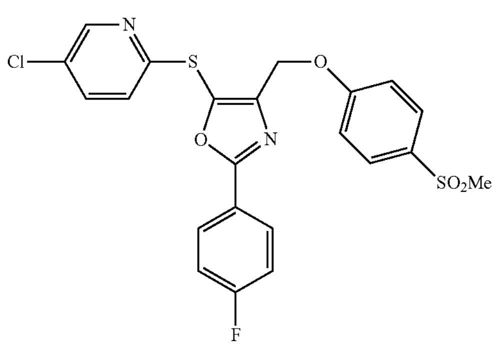 | 5-chloro-2-{[2-(4-fluorophenyl)-4-{[4-(methylsulfonyl)phenoxy]methyl}-1,3-oxazol-5-yl]sulfanyl}pyridine | | 491 |

TABLE B2.1-10-continued

| Ex # | Structure | Name | comments | M + 1 |
|---|---|---|---|---|
| B2.4 | 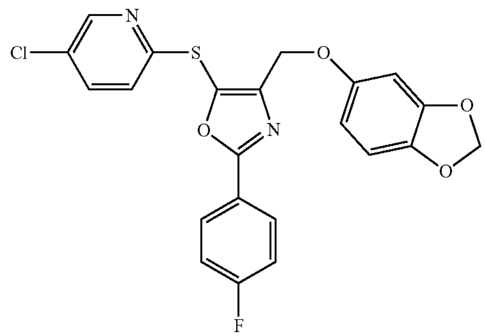 [SMILES: Fc1ccc(-c2nc(COc3ccc4c(c3)OCO4)c(Sc3ccc(Cl)cn3)o2)cc1] | 2-({4-[(1,3-benzodioxol-5-yloxy)methyl]-2-(4-fluorophenyl)-1,3-oxazol-5-yl}sulfanyl)-5-chloropyridine | | 457 |
| B2.5 | 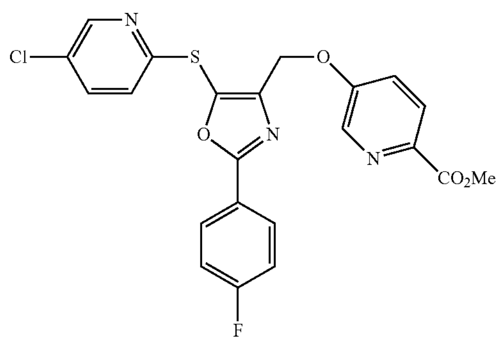 [SMILES: COC(=O)c1ccc(OCc2nc(-c3ccc(F)cc3)oc2Sc2ccc(Cl)cn2)cn1] | methyl 5-({5-[(5-chloropyridin-2-yl)sulfanyl]-2-(4-fluorophenyl)-1,3-oxazol-4-yl}methoxy)pyridine-2-carboxylate | | 472 |
| B2.6 | 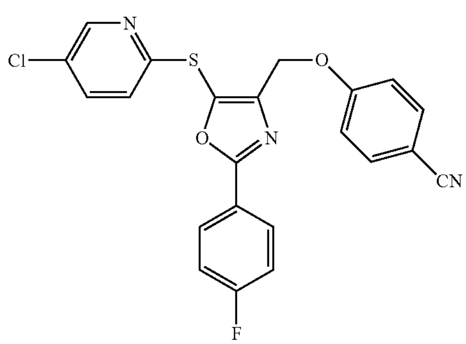 [SMILES: N#Cc1ccc(OCc2nc(-c3ccc(F)cc3)oc2Sc2ccc(Cl)cn2)cc1] | 4-({5-[(5-chloropyridin-2-yl)sulfanyl]-2-(4-fluorophenyl)-1,3-oxazol-4-yl}methoxy)benzonitrile | | 438 |
| B2.7 | 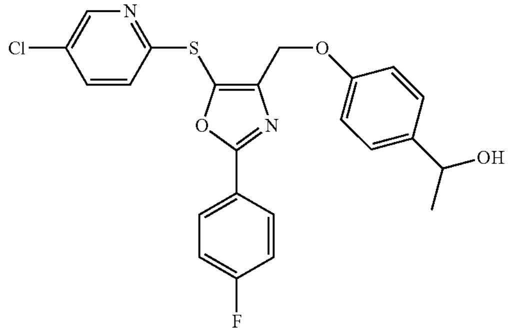 [SMILES: CC(O)c1ccc(OCc2nc(-c3ccc(F)cc3)oc2Sc2ccc(Cl)cn2)cc1] | 1-[4-({5-[(5-chloropyridin-2-yl)sulfanyl]-2-(4-fluorophenyl)-1,3-oxazol-4-yl}methoxy)phenyl]ethanol | Mistsunobu w/4-carboxaldehyde-phenol, followed by MeMgBr addition | 457 |

TABLE B2.1-10-continued

| Ex # | Structure | Name | comments | M + 1 |
|---|---|---|---|---|
| B2.8 | 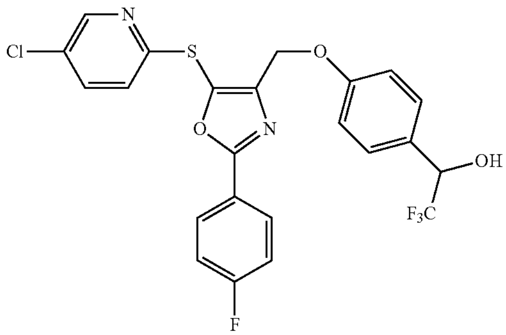 [SMILES: OC(c1ccc(OCc2nc(-c3ccc(F)cc3)oc2Sc2ccc(Cl)cn2)cc1)C(F)(F)F] | 1-[4-({5-[(5-chloropyridin-2-yl)sulfanyl]-2-(4-fluorophenyl)-1,3-oxazol-4-yl}methoxy)phenyl]-2,2,2-trifluoroethanol | Mistsunobu w/4-carboxaldehyde-phenol, followed by CF₃TMS addition | 511 |
| B2.9 | 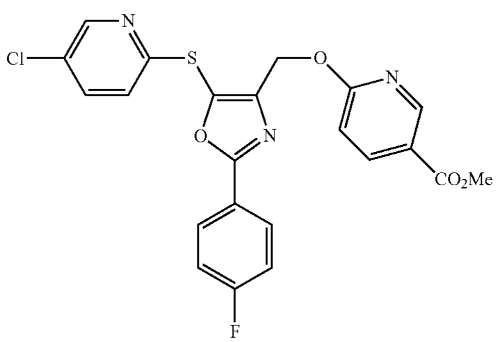 [SMILES: COC(=O)c1ccc(OCc2nc(-c3ccc(F)cc3)oc2Sc2ccc(Cl)cn2)nc1] | methyl 6-({5-[(5-chloropyridin-2-yl)sulfanyl]-2-(4-fluorophenyl)-1,3-oxazol-4-yl}methoxy)pyridine-3-carboxylate | | 472 |
| B2.10 | 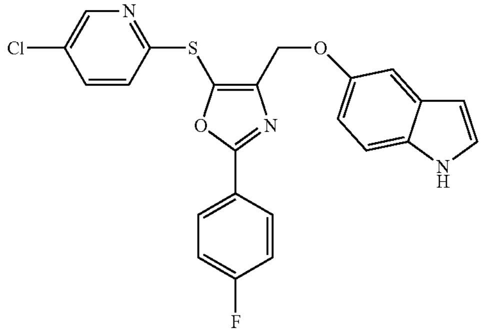 [SMILES: Fc1ccc(-c2nc(COc3ccc4[nH]ccc4c3)c(Sc3ccc(Cl)cn3)o2)cc1] | 5-({5-[(5-chloropyridin-2-yl)sulfanyl]-2-(4-fluorophenyl)-1,3-oxazol-4-yl}methoxy)-1H-indole | | 452 |

Example B2.11

Methyl-4-({5-[(5-chloropyridin-2-yl)sulfanyl]-2-(4-fluorophenyl)-1,3-oxazol-4-yl}methoxy)benzoate

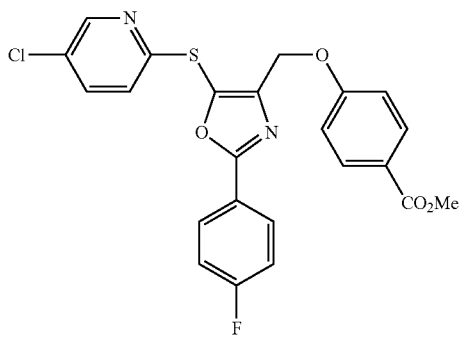 [SMILES: COC(=O)c1ccc(OCc2nc(-c3ccc(F)cc3)oc2Sc2ccc(Cl)cn2)cc1]

Prepared from {5-[(5-chloropyridin-2-yl)sulfanyl]-2-(4-fluorophenyl)-1,3-oxazol-4-yl}methanol (INTERMEDIATE B1.1) and 4-carbomethoxyphenol using a similar procedure as described in the preparation of example B2.1. MS: M+H=471.

Example B2.11.1

4-({5-[(5-chloropyridin-2-yl)sulfanyl]-2-(4-fluorophenyl)-1,3-oxazol-4-yl}methoxy)benzoic acid

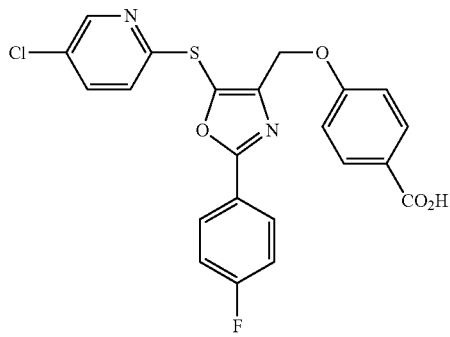 [SMILES: O=C(O)c1ccc(OCc2nc(-c3ccc(F)cc3)oc2Sc2ccc(Cl)cn2)cc1]

To a solution of Methyl-4-({5-[(5-chloropyridin-2-yl)sulfanyl]-2-(4-fluorophenyl)-1,3-oxazol-4-yl}methoxy)benzoate (0.31 g, 0.66 mmol) in 6 ml of 1:1 MeOH/THF was added 1N LiOH (1.98 ml, 1.98 mmol). The reaction was allowed to proceed at 55° C. for 2 h, at which point it was cooled to room temperature and was acidified by 3N HCl. The reaction mixture was diluted with water and extracted with EtOAc. The combined organics were washed with brine, dried over $Na_2SO_4$, filtered and concentrated to yield 4-({5-[(5-chloropyridin-2-yl)sulfanyl]-2-(4-fluorophenyl)-1,3-oxazol-4-yl}methoxy)benzoic acid as a white solid. It was used as is for the next step. LCMS [M+H]=457.3.

Example B2.11.2

4-({5-[(5-chloropyridin-2-yl)sulfanyl]-2-(4-fluorophenyl)-1,3-oxazol-4-yl}methoxy)-N-ethylbenzamide

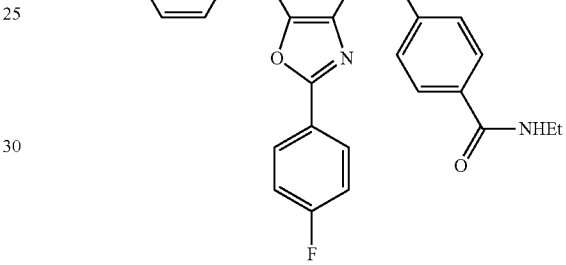

To a solution of 4-({5-[(5-chloropyridin-2-yl)sulfanyl]-2-(4-fluorophenyl)-1,3-oxazol-4-yl}methoxy)benzoic acid (0.48 g, 1.05 mmol), ethylamine hydrochloride (0.09 g, 1.05 mmol) and DIPEA (0.55 ml, 3.15 mmol) in 9 mL of DMF was added BOP (0.56 g, 1.26 mmol). It was stirred at room temperature for 2 h. Water was added and extracted with EA. The organic layers were combined and washed with 3M LiCl (3×), dried over $Na_2SO_4$, filtered and concentrated. The reaction was purified by flash chromatography (silica, 30-70% EtOAc/hexanes) to give 4-({5-[(5-chloropyridin-2-yl)sulfanyl]-2-(4-fluorophenyl)-1,3-oxazol-4-yl}methoxy)-N-ethylbenzamide: $^1$H NMR (400 MHz, CDCl$_3$) δ 8.35 (d, J=2.5 Hz, 1H), 8.08 (m, 2H), 7.66 (d, J=8.7 Hz, 2H), 7.48 (dd, J=8.4, 2.6 Hz, 1H), 7.15 (m, 2H), 6.96 (m, 3H), 5.95 (s, 1H), 5.15 (s, 2H), 3.45 (m, 2H), 1.22 (t, J=7.3 Hz, 3H); HRMS exact mass calc for C24H19ClFN3O3S [M+H]$^+$: 484.0892; observed: 484.0900.

Examples in Table B2.11.2-5 are prepared from 4-({5-[(5-chloropyridin-2-yl)sulfanyl]-2-(4-fluorophenyl)-1,3-oxazol-4-yl}methoxy)benzoic acid (EXAMPLE B2.11.1) and the appropriate amine, using a procedure similar as described in the preparation of 4-({5-[(5-chloropyridin-2-yl)sulfanyl]-2-(4-fluorophenyl)-1,3-oxazol-4-yl}methoxy)-N-ethylbenzamide (EXAMPLE B2.11.2).

TABLE B.2.11.2-5

| Ex # | Structure | Name | M + 1 |
|---|---|---|---|
| B2.11.2 | 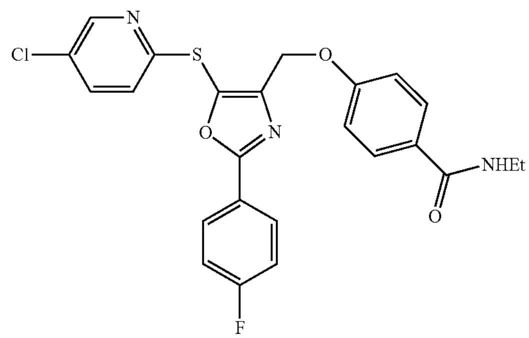 | 4-({5-[(5-chloropyridin-2-yl)sulfanyl]-2-(4-fluorophenyl)-1,3-oxazol-4-yl}methoxy)-N-ethylbenzamide | 484 |
| B2.11.3 | 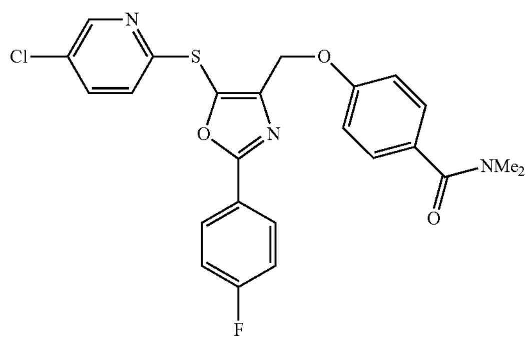 [SMILES: CN(C)C(=O)c1ccc(OCc2nc(-c3ccc(F)cc3)oc2Sc2ccc(Cl)cn2)cc1] | 4-({5-[(5-chloropyridin-2-yl)sulfanyl]-2-(4-fluorophenyl)-1,3-oxazol-4-yl}methoxy)-N,N-dimethylbenzamide | 484 |
| B2.11.4 | 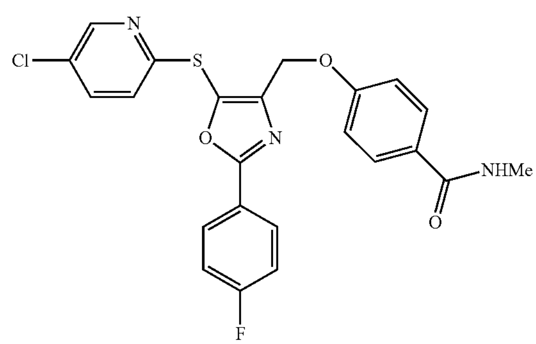 [SMILES: CNC(=O)c1ccc(OCc2nc(-c3ccc(F)cc3)oc2Sc2ccc(Cl)cn2)cc1] | 4-({5-[(5-chloropyridin-2-yl)sulfanyl]-2-(4-fluorophenyl)-1,3-oxazol-4-yl}methoxy)-N-methylbenzamide | 470 |
| B2.11.5 | 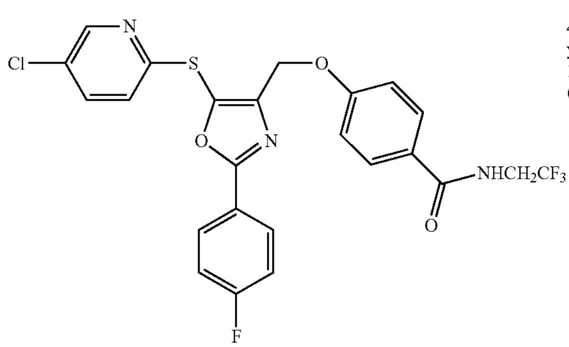 | 4-({5-[(5-chloropyridin-2-yl)sulfanyl]-2-(4-fluorophenyl)-1,3-oxazol-4-yl}methoxy)-N-(2,2,2-trifluoroethyl)benzamide | 538 |

Example B2.12

5-chloro-2-{[2-(4-fluorophenyl)-4-{[(1-methyl-1H-1,2,4-triazol-5-yl)methoxy]methyl}-1,3-oxazol-5-yl]sulfanyl}pyridine

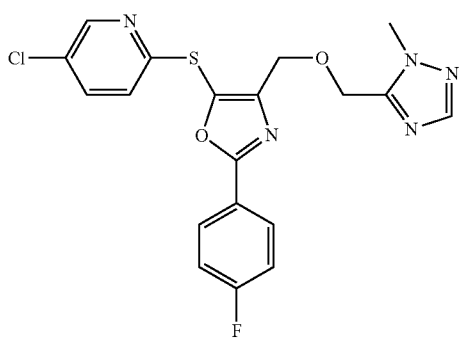 [SMILES: Cn1ncnc1COCc1nc(-c2ccc(F)cc2)oc1Sc1ccc(Cl)cn1]

To a solution of 2-methyl-2H-[1,2,4]triazole-3-yl)-methanol (0.01 g, 0.08 mmol) in 0.3 ml of DMF was added 1M NaHMDS in THF (0.09 ml, 0.09 mmol). After 10 min at rt, 2-{[4-(bromomethyl)-2-(4-fluorophenyl)-1,3-oxazol-5-yl]sulfanyl}-5-chloropyridine (0.03 g, 0.08 mmol) in 0.2 ml of DMF was added. After 3 h, a drop of water was added to the reaction and purified by reverse phase HPLC to give 20 mg of 5-chloro-2-{[2-(4-fluorophenyl)-4-{[(1-methyl-1H-1,2,4-triazol-5-yl)methoxy]methyl}-1,3-oxazol-5-yl]sulfanyl}pyridine. $^1$H NMR (400 MHz, CD$_3$OD) δ 8.37 (d, J=2.5 Hz, 1H), 8.09 (m, 2H), 7.91 (s, 1H), 7.71 (dd, J=8.6, 2.5 Hz, 1H), 7.21 (m, 3H), 4.80 (s, 2H), 4.66 (s, 2H), 3.91 (s, 3H); HRMS exact mass calc for C19H15ClFN5O2S [M+H]$^+$: 432.0692; observed: 432.0689.

Examples in Table B.212-15 are prepared from 2-{[4-(bromomethyl)-2-(4-fluorophenyl)-1,3-oxazol-5-yl]sulfanyl}-5-chloropyridine (INTERMEDIATE B3.1) and the appropriate alcohol, using a procedure similar as described in the preparation of 5-chloro-2-{[2-(4-fluorophenyl)-4-{[(1-methyl-1H-1,2,4-triazol-5-yl)methoxy]methyl}-1,3-oxazol-5-yl]sulfanyl}pyridine (EXAMPLE B2.12).

TABLE B.2.12-15

| Ex # | Structure | Name | comments | M + 1 |
|---|---|---|---|---|
| B2.12 | 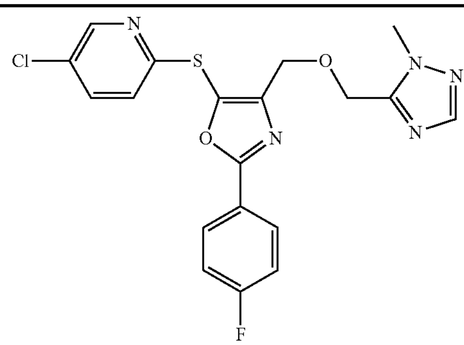 | 5-chloro-2-{[2-(4-fluorophenyl)-4-{[(1-methyl-1H-1,2,4-triazol-5-yl)methoxy]methyl}-1,3-oxazol-5-yl]sulfanyl}pyridine | | 432 |
| B2.13 | 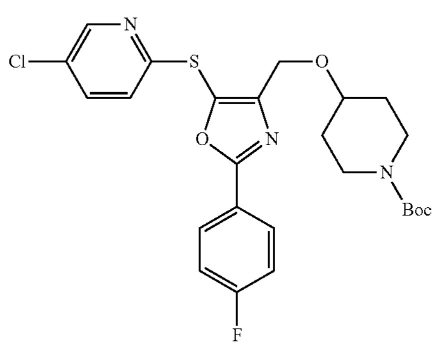 [SMILES: CC(C)(C)OC(=O)N1CCC(OCc2nc(-c3ccc(F)cc3)oc2Sc2ccc(Cl)cn2)CC1] | tert-butyl 4-({5-[(5-chloropyridin-2-yl)sulfanyl]-2-(4-fluorophenyl)-1,3-oxazol-4-yl}methoxy)piperidine-1-carboxylate | | 520 |
| B2.14 | 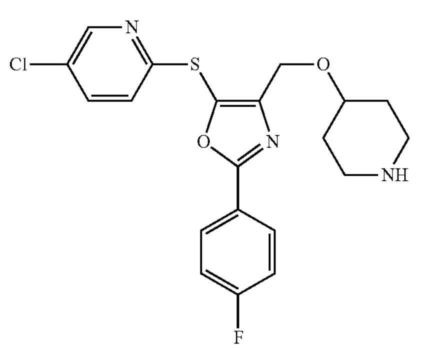 [SMILES: Fc1ccc(-c2nc(COC3CCNCC3)c(Sc3ccc(Cl)cn3)o2)cc1] | 5-chloro-2-({2-(4-fluorophenyl)-4-[(piperidin-4-yloxy)methyl]-1,3-oxazol-5-yl}sulfanyl)pyridine | Boc removal from example B2.13 | 420 |

TABLE B.2.12-15-continued

| Ex # | Structure | Name | comments | M + 1 |
|---|---|---|---|---|
| B2.15 | 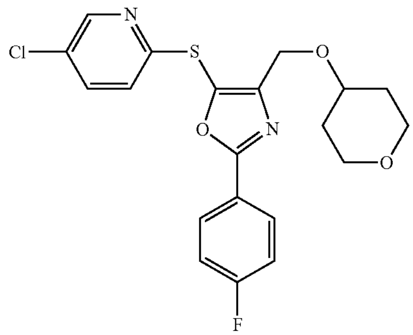 [SMILES: Fc1ccc(-c2nc(COC3CCOCC3)c(Sc3ccc(Cl)cn3)o2)cc1] | 5-chloro-2-({2-(4-fluorophenyl)-4-[(tetrahydro-2H-pyran-4-yloxy)methyl]-1,3-oxazol-5-yl}sulfanyl)pyridine | | 421 |

Example B2.16

6-({5-[(5-chloropyridin-2-yl)sulfanyl]-2-(4-fluorophenyl)-1,3-oxazol-4-yl}methoxy)-N-ethylpyridine-3-carboxamide

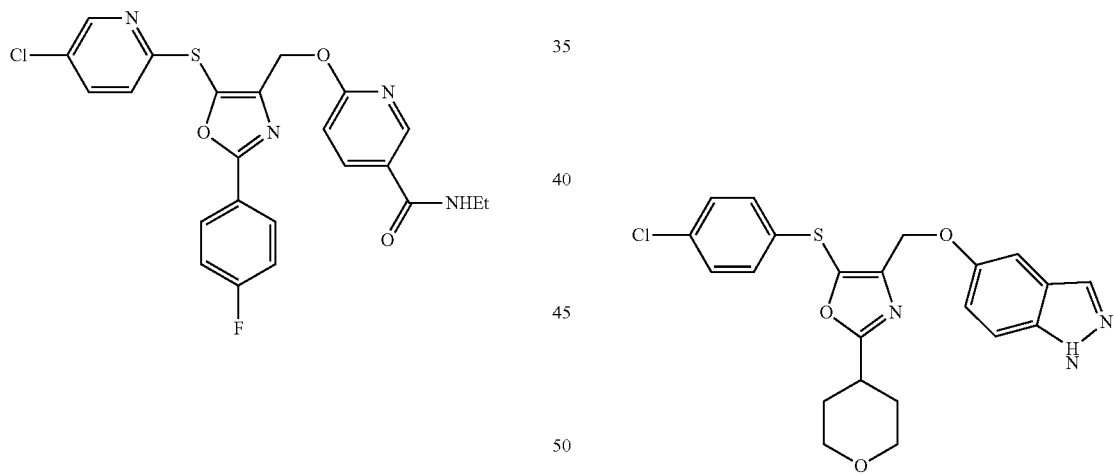

To a solution of {5-[(5-chloropyridin-2-yl)sulfanyl]-2-(4-fluorophenyl)-1,3-oxazol-4-yl}methanol (intermediate B1.1, 0.03 g, 0.09 mmol) in 0.6 ml of THF was added 1M NaHMDS in THF (0.11 ml, 0.11 mmol). After 10 min at rt, 6-bromo-N-ethylnicotinamide (0.02 g, 0.08 mmol) was added. After 3 h, a drop of water was added to the reaction and purified by reverse phase HPLC to give 6-({5-[(5-chloropyridin-2-yl)sulfanyl]-2-(4-fluorophenyl)-1,3-oxazol-4-yl}methoxy)-N-ethylpyridine-3-carboxamide. $^1$H NMR (400 MHz, CDCl$_3$) δ 8.43 (d, J=2.4 Hz, 1H), 8.35 (d, J=2.4 Hz, 1H), 8.08 (m, 2H), 7.96 (dd, J=8.6, 2.6 Hz, 1H), 7.48 (dd, J=8.4, 2.6 Hz, 1H), 7.13 (m, 2H), 6.96 (d, J=8.4 Hz, 1H), 6.8 (d, J=8.8 Hz, 1H), 5.94 (s, 1H), 5.48 (s, 2H), 3.46 (m, 2H), 1.24 (t, J=7.3 Hz, 3H); HRMS exact mass calc for C23H18ClFN4O3S [M+H]$^+$: 485.0845; observed: 485.0854.

Example B2.17

5-({5-[(4-chlorophenyl)sulfanyl]-2-(tetrahydro-2H-pyran-4-yl)-1,3-oxazol-4-yl}methoxy)-1H-indazole Prepared from {5-[(4-chlorophenyl)sulfanyl]-2-(tetrahydro-2H-pyran-4-yl)-1,3-oxazol-4-yl}methanol (INTERMEDIATE C6.1) and 1H-indazol-5-ol using a similar procedure as described in the preparation of example B2.1. MS: M+H=442.

Example B5.1 methyl 4-[({5-[(5-chloropyridin-2-yl)sulfanyl]-2-(4-fluorophenyl)-1,3-oxazol-4-yl}methyl)amino]benzoate

Example B5.2 methyl 4-[({5-[(5-chloropyridin-2-yl)sulfanyl]-2-(4-fluorophenyl)-1,3-oxazol-4-yl}methyl)(methyl)amino]benzoate

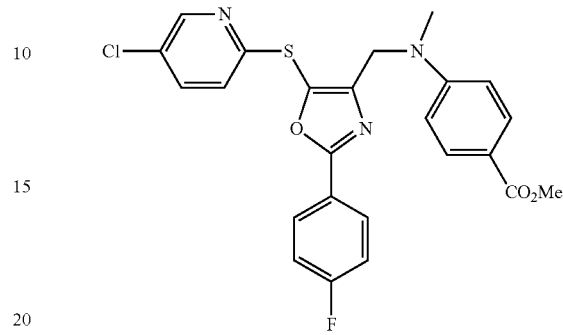

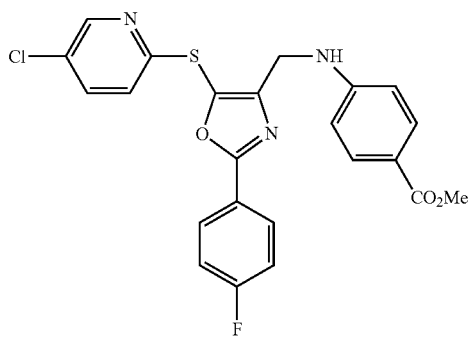 [SMILES: COC(=O)c1ccc(NCc2nc(-c3ccc(F)cc3)oc2Sc2ccc(Cl)cn2)cc1]

To a solution of 5-[(5-chloropyridin-2-yl)sulfanyl]-2-(4-fluorophenyl)-1,3-oxazole-4-carbaldehyde (intermediate B4:1, 0.02 g, 0.06 mmol) in DCE was added methyl 4-aminobenzoate (0.01 g, 0.06 mmol), acetic acid (3.4 ul, 0.06 mmol) and NaBH(OAc)$_3$ (0.015 g, 0.07 mmol). After Stirring at rt overnight, a drop of water was added to the reaction and purified by reverse phase HPLC to give methyl 4-[({5-[(5-chloropyridin-2-yl)sulfanyl]-2-(4-fluorophenyl)-1,3-oxazol-4-yl}methyl)amino]benzoate. $^1$H NMR (400 MHz, CDCl$_3$) δ 8.35 (d, J=2.5 Hz, 1H), 8.05 (m, 2H), 737 (d, J=8.8 Hz, 2H), 7.44 (dd, J=8.4, 2.5 Hz, 1H), 7.14 (m, 2H), 6.90 (d, J=8.4 Hz, 1H), 6.61 (d, 3=8.8 Hz, 2H), 4.43 (s, 2H), 3.84 (s, 3H); HRMS exact mass calc for C23H17ClFN3O3S [M+H]: 470.0736; observed: 470.0734.

A solution of 2-{[4-(bromomethyl)-2-(4-fluorophenyl)-1,3-oxazol-5-yl]sulfanyl}-5-chloropyridine (intermediate B3.1, 0.03 g, 0.075 mmol), methyl 4-methylaminobenzoate (0.013 g, 0.08 mmol) and K$_2$CO$_3$ (0.03 g, 0.225 mmol) in DMF was heated at 65° C. for 2 hr, filtered and purified by reverse phase HPLC to give methyl 4-[({5-[(5-chloropyridin-2-yl)sulfanyl]-2-(4-fluorophenyl)-1,3-oxazol-4-yl}methyl)(methyl)amino]benzoate. $^1$H NMR (400 MHz, CDCl$_3$) δ 8.31 (d, J=2.5 Hz, 1H), 8.03 (m, 2H), 7.72 (d, J=9.2 Hz, 2H), 7.34 (dd, J=8.4, 2.5 Hz, 1H), 7.13 (m, 2H), 6.70 (m, 3H), 4.62 (s, 2H), 3.84 (s, 3H), 3.17 (s, 3H); HRMS exact mass calc for C24H19ClFN3O3S [M+H]$^+$: 484.0892; observed: 484.0890.

Examples in Table B.5.1-14 are prepared from reductive amination of 5-[(5-chloropyridin-2-yl)sulfanyl]-2-(4-fluorophenyl)-1,3-oxazole-4-carbaldehyde (INTERMEDIATE B4.1), or from 5-[(4-chlorophenyl)sulfanyl]-2-(tetrahydro-2H-pyran-4-yl)-1,3-oxazole-4-carbaldehyde (INTERMEDIATE C5.1), with appropriate aniline using a procedure similar as described in the preparation of methyl 4-[({5-[(5-chloropyridin-2-yl)sulfanyl]-2-(4-fluorophenyl)-1,3-oxazol-4-yl}methyl)amino]benzoate (EXAMPLE B5.1) or from alkylation of 2-{[4-(bromomethyl)-2-(4-fluorophenyl)-1,3-oxazol-5-yl]sulfanyl}-5-chloropyridine (INTERMEDIATE B3.1) with aniline, using a procedure similar as described in the preparation of methyl 4-[({5-[(5-chloropyridin-2-yl)sulfanyl]-2-(4-fluorophenyl)-1,3-oxazol-4-yl}methyl)(methyl)amino]benzoate (EXAMPLE B5.2).

TABLE B5.1-14

| Ex # | Structure | Name | comments | M + 1 |
| --- | --- | --- | --- | --- |
| B5.1 | 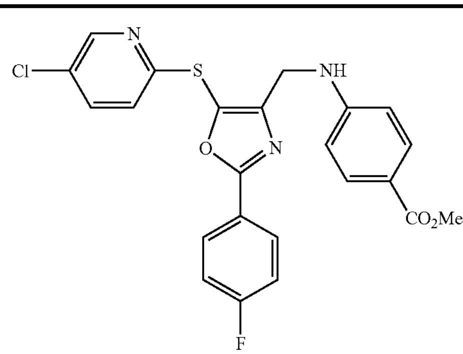 | methyl 4-[({5-(5-chloropyridin-2-yl)sulfanyl]-2-(4-fluorophenyl)-1,3-oxazol-4-yl}methyl)amino]benzoate | From aldehyde B4.1 | 470 |

TABLE B5.1-14-continued

| Ex # | Structure | Name | comments | M + 1 |
|---|---|---|---|---|
| B5.2 | 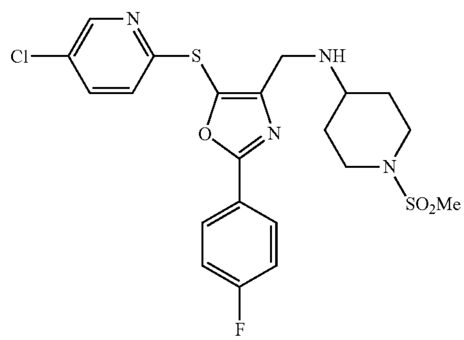 [SMILES: CS(=O)(=O)N1CCC(NCc2nc(-c3ccc(F)cc3)oc2Sc2ccc(Cl)cn2)CC1] | methyl 4-[({5-[(5-chloropyridin-2-yl)sulfanyl]-2-(4-fluorophenyl)-1,3-oxazol-4-yl}methyl)(methyl)amino]benzoate | From aldehyde B4.1 | 498 |
| B5.3 | 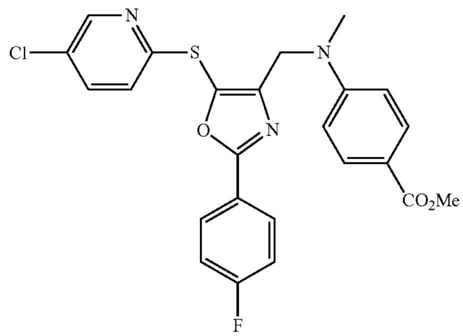 | methyl 4-[({5-[(5-chloropyridin-2-yl)sulfanyl]-2-(4-fluorophenyl)-1,3-oxazol-4-yl}methyl)(methyl)amino]benzoate | From bromide B3.1 | 484 |
| B5.4 | 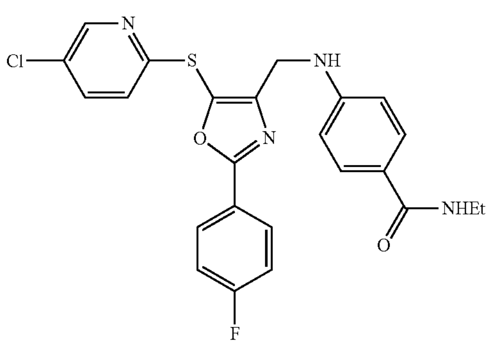 | 4-[({5-[(5-chloropyridin-2-yl)sulfanyl]-2-(4-fluorophenyl)-1,3-oxazol-4-yl}methyl)amino]-N-ethylbenzamide | From bromide B3.1 | 483 |
| B5.5 | 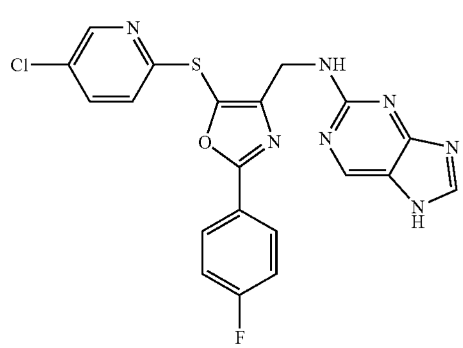 [SMILES: Fc1ccc(-c2nc(CNc3ncc4[nH]cnc4n3)c(Sc3ccc(Cl)cn3)o2)cc1] | N-({5-[(5-chloropyridin-2-yl)sulfanyl]-2-(4-fluorophenyl)-1,3-oxazol-4-yl}methyl)-7H-purin-2-amine | From bromide B3.1 | 454 |

TABLE B5.1-14-continued

| Ex # | Structure | Name | comments | M + 1 |
|---|---|---|---|---|
| B5.6 | 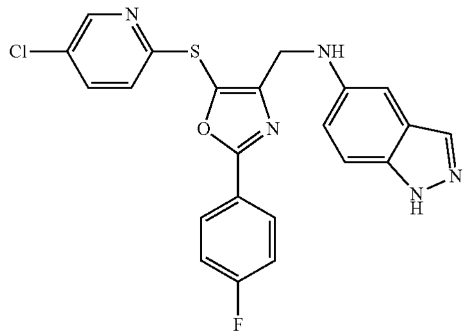 [SMILES: Fc1ccc(-c2nc(CNc3ccc4[nH]ncc4c3)c(Sc3ccc(Cl)cn3)o2)cc1] | N-({5-[(5-chloropyridin-2-yl)sulfanyl]-2-(4-fluorophenyl)-1,3-oxazol-4-yl}methyl)-1H-indazol-5-amine | From bromide B3.1 | 452 |
| B5.7 | 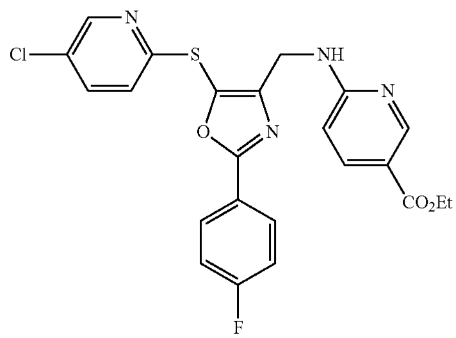 [SMILES: CCOC(=O)c1ccc(NCc2nc(-c3ccc(F)cc3)oc2Sc2ccc(Cl)cn2)nc1] | ethyl 6-[({5-[(5-chloropyridin-2-yl)sulfanyl]-2-(4-fluorophenyl)-1,3-oxazol-4-yl}methyl)amino]pyridine-3-carboxylate | From bromide B3.1 | 485 |
| B5.8 | 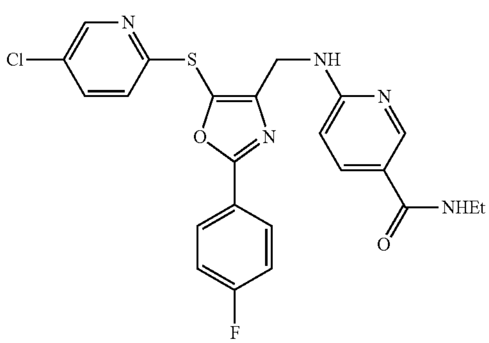 | 6-[({5-[(5-chloropyridin-2-yl)sulfanyl]-2-(4-fluorophenyl)-1,3-oxazol-4-yl}methyl)amino]-N-ethylpyridine-3-carboxamide | Hydrolysis of example B5.6 followed by ethylamine coupling | 484 |
| B5.9 | 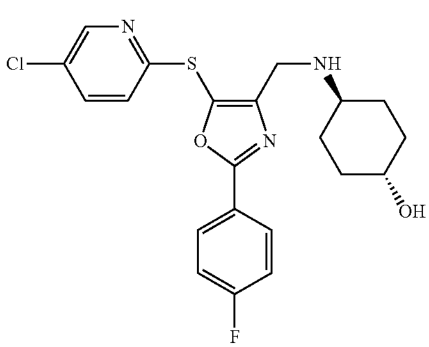 [SMILES: O[C@H]1CC[C@H](NCc2nc(-c3ccc(F)cc3)oc2Sc2ccc(Cl)cn2)CC1] | trans-4-[({5-[(5-chloropyridin-2-yl)sulfanyl]-2-(4-fluorophenyl)-1,3-oxazol-4-yl}methyl)amino]cyclohexanol | From bromide B3.1 | 434 |

TABLE B5.1-14-continued

| Ex # | Structure | Name | comments | M + 1 |
|---|---|---|---|---|
| B5.10 | 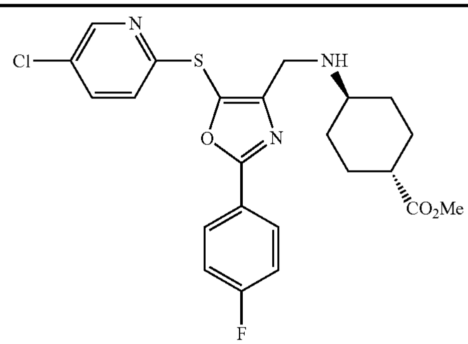 | methyl trans-4-{({5-[(5-chloropyridin-2-yl)sulfanyl]-2-(4-fluorophenyl)-1,3-oxazol-4-yl}methyl)amino]cyclohexanecarboxylate | From bromide B3.1 | 476 |
| B5.11 | 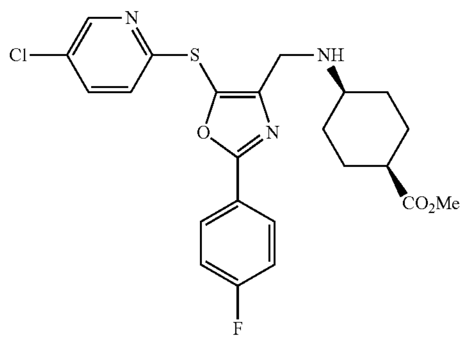 [SMILES: COC(=O)[C@H]1CC[C@@H](NCc2nc(-c3ccc(F)cc3)oc2Sc2ccc(Cl)cn2)CC1] | methyl cis-4-[({5-[(5-chloropyridin-2-yl)sulfanyl]-2-(4-fluorophenyl)-1,3-oxazol-4-yl}methyl)amino]cyclohexanecarboxylate | From bromide B3.1 | 476 |
| B5.12 | 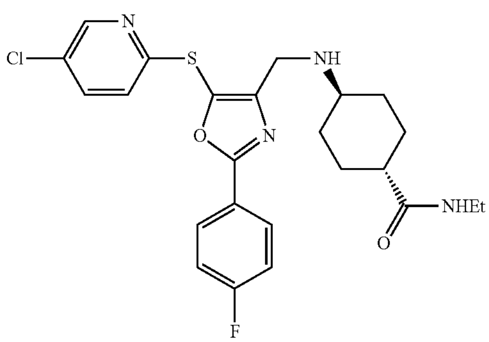 | trans-4-[({5-[(5-chloropyridin-2-yl)sulfanyl]-2-(4-fluorophenyl)-1,3-oxazol-4-yl}methyl)amino]-N-ethylcyclohexanecarboxamide | Hydrolysis of B5.10 and coupling of ethylamine | 490 |
| B5.13 | 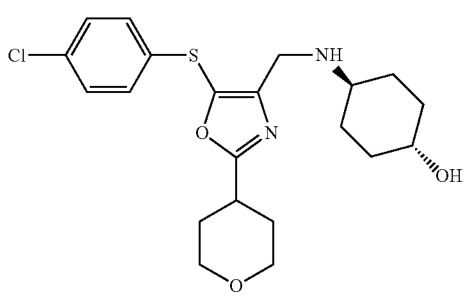 [SMILES: O[C@H]1CC[C@H](NCc2nc(C3CCOCC3)oc2Sc2ccc(Cl)cc2)CC1] | trans-4-[({5-[(4-chlorophenyl)sulfanyl]-2-(tetrahydro-2H-pyran-4-yl)-1,3-oxazol-4-yl}methyl)amino]cyclohexanol | From aldehyde C5.1 | 423 |
| B5.14 | 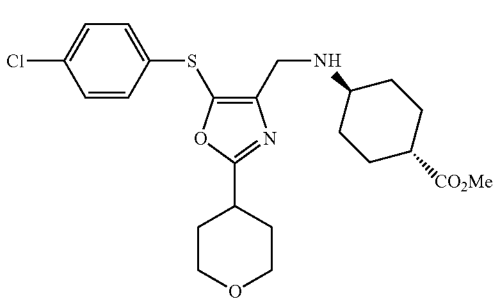 [SMILES: COC(=O)[C@H]1CC[C@H](NCc2nc(C3CCOCC3)oc2Sc2ccc(Cl)cc2)CC1] | methyl trans-4-[({5-[(4-chlorophenyl)sulfanyl]-2-(tetrahydro-2H-pyran-4-yl)-1,3-oxazol-4-yl}methyl)amino]cyclohexanecarboxylate | From aldehyde C5.1 | 466 |

Example B7.1 methyl 4-(1-{5-[(5-chloropyridin-2-yl)sulfanyl]-2-(4-fluorophenyl)-1,3-oxazol-4-yl}ethoxy)benzoate

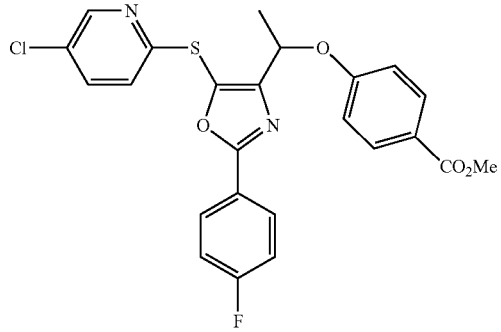 [SMILES: COC(=O)c1ccc(OC(C)c2nc(-c3ccc(F)cc3)oc2Sc2ccc(Cl)cn2)cc1]

Prepared from 1-{5-[(5-chloropyridin-2-yl)sulfanyl]-2-(4-fluorophenyl)-1,3-oxazol-4-yl}ethanol (INTERMEDIATE B6.1) and 4-carbomethoxyphenol using a similar procedure as described in the preparation of example B2.1. MS: M+H=485.

Example B7.2

4-(1-{5-[(5-chloropyridin-2-yl)sulfanyl]-2-(4-fluorophenyl)-1,3-oxazol-4-yl}ethoxy)-N-methylbenzamide

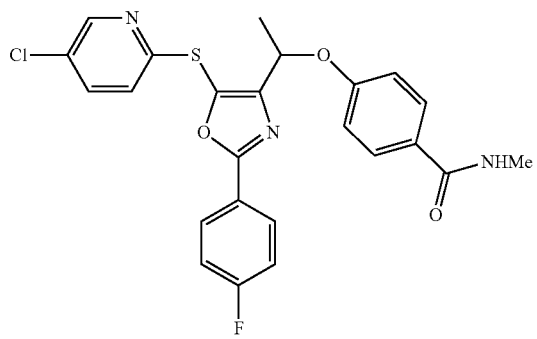 [SMILES: CNC(=O)c1ccc(OC(C)c2nc(-c3ccc(F)cc3)oc2Sc2ccc(Cl)cn2)cc1]

Prepared from hydrolysis of methyl 4-(1-{5-[(5-chloropyridin-2-yl)sulfanyl]-2-(4-fluorophenyl)-1,3-oxazol-4-yl}ethoxy)benzoate (EXAMPLE 137.1) followed by methylamine coupling, using a similar procedure as described in the preparation of examples 132.11.1 and B2.11.2. MS: M+H=484.

Example D4.1 methyl 4-({5-[(5-chloropyridin-2-yl)sulfanyl]-2-cyclopropyl-1,3-oxazol-4-yl}methoxy)benzoate

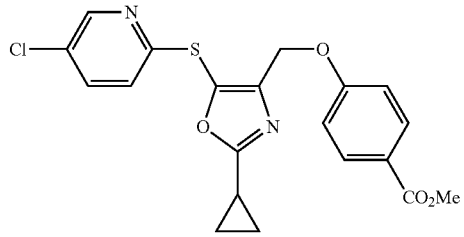 [SMILES: COC(=O)c1ccc(OCc2nc(C3CC3)oc2Sc2ccc(Cl)cn2)cc1]

To a solution of (5-bromo-2-cyclopropyl-1,3-oxazol-4-yl)methanol (intermediate D3.1, 0.10 g, 0.46 mmol) in THF (4 ml) was added 4-carbomethoxyphenol (0.11 g, 0.69 mmol), $Ph_3P$ (0.18 g, 0.69 mmol) and DIAD (0.13 ml, 0.69 mmol). After 2 h at rt, the reaction was concentrated and purified by flash chromatography (silica, 0-35% EtOAc/hexanes) to give methyl 4-[(5-bromo-2-cyclopropyl-1,3-oxazol-4-yl)methoxy]benzoate. LCMS $[M+H]^+=352.2$.

An oven-dried flask was charged with CuI (0.004 g, 0.02 mmol), 5-chloropyridine-2-thiol (0.015 g, 0.10 mmol), N,N-dimethylglycine (0.002 g, 0.02 mmol) and $K_3PO_4$ (0.048 g, 0.23 mmol), evacuated and backfilled with $N_2$. Methyl 4-[(5-bromo-2-cyclopropyl-1,3-oxazol-4-yl)methoxy]benzoate (0.036 g, 0.10 mmol) and DMF (0.5 ml) was added under $N_2$. The reaction mixture was heated at 120° C. overnight. The reaction was cooled to rt and filtered through a pad of silica gel eluting with EtOAc. The filtrate was concentrated and purified by reverse phase HPLC to give methyl 4-({5-[(5-chloropyridin-2-yl)sulfanyl]-2-cyclopropyl-1,3-oxazol-4-yl}methoxy)benzoate. $^1$H NMR (400 MHz, $CDCl_3$) δ 8.36 (d, J=2.5 Hz, 1H), 7.90 (d, J=8.7, 2H), 7.48 (dd, J=8.4, 2.5 Hz, 1H), 6.95 (d, 3=8.7 Hz, 2H), 6.87 (d, J=8.4 Hz, 1H), 5.05 (s, 2H), 3.88 (s, 3H), 2.12 (m, 1H), 1.10 (m, 4H); FIRMS exact mass calc for C20H17ClN2O4S $[M+H]^+$: 417.0670; observed: 417.0671.

Example D4.2

5-({5-[(5-chloropyridin-2-yl)sulfanyl]-2-cyclopropyl-1,3-oxazol-4-yl}methoxy)-1H-indazole

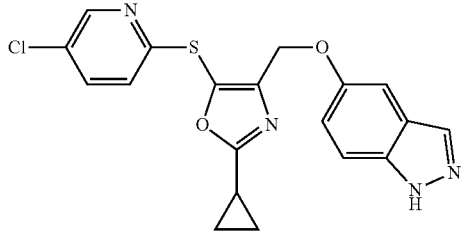 [SMILES: Clc1ccc(Sc2oc(C3CC3)nc2COc2ccc3[nH]ncc3c2)nc1]

Prepared from (5-bromo-2-cyclopropyl-1,3-oxazol-4-yl)methanol (INTERMEDIATE D3.1) and 1H-indazol-5-ol using a similar procedure as described in the preparation of example D4.1. MS: M+H=399.

What is claimed is:

1. A compound of the formula I:

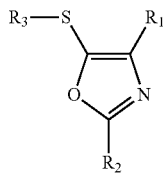

or a pharmaceutically acceptable salt thereof wherein:

$R_1$ is

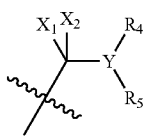

n is 0, 1 or 2;

$X_1$ and $X_2$ are each independently selected from hydrogen, and $C_{1-4}$ alkyl optionally mono, di- or tri-substituted with fluoro, or $X_1$ and $X_2$ taken together form an oxo group;

Y is selected from O and —N;

$R_4$ is a heterocycle with two to four heteroatoms selected from O, S and N:

wherein $R_4$ is optionally mono or di-substituted with substituents independently selected from the group consisting of:
(a) halo,
(b) —CN,
(c) mono, di or tri-halo —$C_{1-4}$ alkyl,
(d) OH,
(e) mono, di or tri-halo —$OC_{1-4}$ alkyl,
(f) —$OC_{1-4}$ alkyl, optionally substituted with hydroxyl, halo or amino,
(g) —$C_{1-4}$alkyl optionally substituted with one or two substituents selected from hydroxyl, CN, —$CHF_2$ and —$CF_3$,
(h) —$C_{1-2}$alkyl-$C_{3-6}$cycloalkyl optionally substituted with hydroxy, halo or CN,
(i) —$S(O)_nC_{1-4}$alkyl,
(j) —$S(O)_nNR^6R^7$,
(k) —C(O)—NH—$NR^8R^9$,
(l) —C(O)—OH,
(m) —C(O)—$OC_{1-4}$alkyl, optionally substituted with halo or hydroxy,
(n) —C(O)—$NR^{10}R^{11}$,
(o) —C(O)—$C_{1-4}$alkyl optionally mono, di or tri substituted with halo,
(p) —$C(NR^{12})$—$NR^{13}R^{14}$,
(q) $HET^4$,
(r) aryl,
(s) —C(O)—NH—NH—C(O)H,
(t) —$CH_2$—C(O)—O—$C_{1-4}$alkyl, whereas the $CH_2$ may be optionally substituted with $C_{1-4}$alkyl or OH
(u) —$CH_2$—C(O)$NR^{15}R^{16}$, whereas the $CH_2$ may be optionally substituted with $C_{1-4}$alkyl or OH, (v) —NR$^{17}$R$^{18}$, and
(w) mono, di or tri-halo C1-4alkyl-NR$^{17}$R$^{18}$,
wherein choices (q) and (r) are each optionally mono or di-substituted with substituents selected from
(1) halo,
(2) —CN,
(3) —OH,
(4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH, and
(8) —C(O)O—C$_{1-3}$alkyl,
(9) —C(O)—NR$^{19}$R$^{20}$,
(10) —NH$_2$,
(11) oxo, and
(12)=S,
wherein R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$ and R$^{20}$, are each independently selected from H and C$_{1-4}$alkyl, wherein said C$_{1-4}$alkyl is optionally substituted with CF$_3$,
or
R$^6$ and R$^7$ or R$^8$ and R$^9$ or R$^{10}$ and R$^{11}$ or R$^{13}$ and R$^{14}$ or R$^{15}$ and R$^{16}$ or R$^{17}$ and R$^{18}$ or R$^{19}$ and R$^{20}$ are joined together to form a ring with the atoms to which they are attached there is formed a heterocyclic ring of 4 to 7 atoms, said ring containing 1, 2, 3 or 4 heteroatoms selected from N, O and S, said ring being optionally mono or di-substituted with substituents independently selected from halo, hydroxyl, oxo, C$_{1-4}$alkyl, hydroxyC$_{1-4}$alkyl, haloC$_{1-4}$alkyl, —C(O)—C$_{1-4}$alkyl and —S(O)$_n$C$_{1-4}$alkyl;
R$_5$ is selected from the group consisting of:
(1) hydrogen
(2) mono, di or tri-halo C$_{1-4}$ alkyl,
(3) aryl,
(4) HET$_1$,
(5) C$_{3-6}$cycloalkyl,
(6) CH$_2$-aryl,
(7) CH$_2$-HET$_1$,
(8) CH$_2$—C$_{3-6}$cycloalkyl,
(9) —C$_{1-4}$alkyl optionally substituted with one or two substituents selected from hydroxyl, CN, —CHF$_2$ and —CF$_3$, and
(10) —C$_{1-2}$alkyl-C$_{3-6}$cycloalkyl optionally substituted with hydroxy, halo or CN,
with the proviso that when Y is O, R$_5$ is not present;
R$^2$ is selected from phenyl or pyridyl:
wherein R$^2$ is optionally mono or di-substituted with substituents independently selected from the group consisting of
(a) halo,
(b) —CN,
(c) —OH,
(d) —NR$_{21}$R$_{22}$, wherein R$_{21}$ and R$_{22}$ are each independently selected from hydrogen and C$_{1-4}$alkyl,
(e) —C$_{1-4}$alkyl optionally substituted with hydroxy, halo or cyano, or amino
(f) —CF$_3$,
(g) —OC$_{1-4}$alkyl optionally substituted with hydroxyl or halo,
(h) —C(O)O—C$_{1-3}$alkyl,
(i) —C(O)NR$_{21}$R$_{22}$, and
(j) —S-aryl, optionally substituted with halo, C$_{1-4}$alkyl or —OC$_{1-4}$alkyl;

R$_3$ is phenyl or pyridyl:
wherein R$_3$ is optionally mono or di-substituted with substituents independently selected from the group consisting of
(a) hydroxy,
(b) halo,
(c) —C$_{3-6}$cycloalkyl,
(d) —OC$_{3-5}$cycloalkyl,
(e) —C$_{1-4}$alkyl,
(f) —OC$_{1-4}$alkyl,
(g) —C(O)CH$_3$
(h) mono, di or tri-halo C$_{1-4}$ alkyl,
(i) mono, di or tri-halo —OC$_{1-4}$ alkyl, and
(j) —S(O)$_n$—C$_{1-4}$alkyl;
wherein aryl is as a mono- or bi-cyclic aromatic ring system; and HET$^1$, HET$^2$, HET$^3$, HET$^4$ and HET$^5$ are each independently a 5 to 10-membered aromatic, partially aromatic or non-aromatic mono- or bicyclic ring, or N-oxide thereof, said containing 1 to 4 heteroatoms selected from O, S and N, and optionally substituted with 1 to 2 oxo groups.

2. A compound selected from the group consisting of

Structure

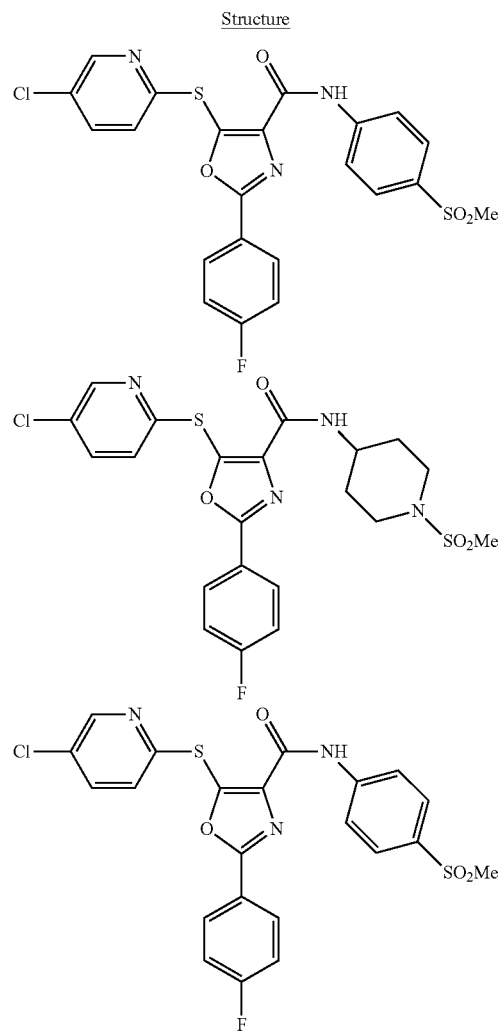

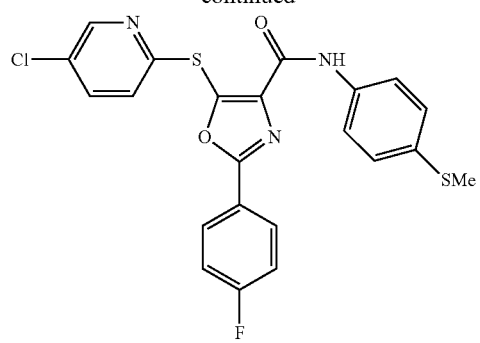
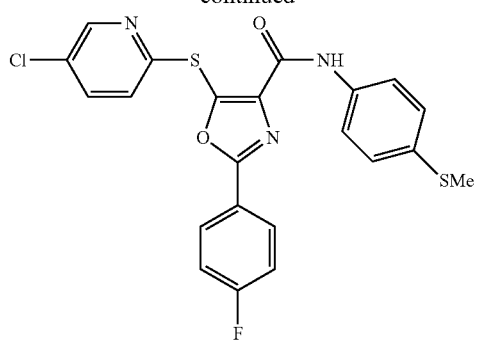
or a pharmaceutically acceptable salt thereof.
3. A compound selected from the group consisting of
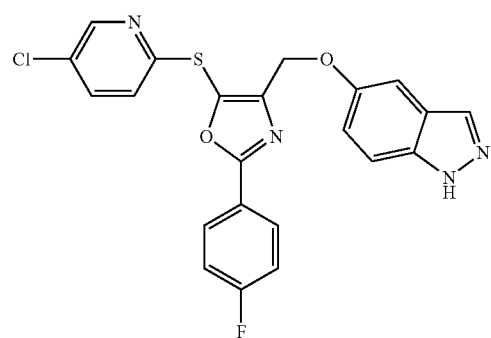
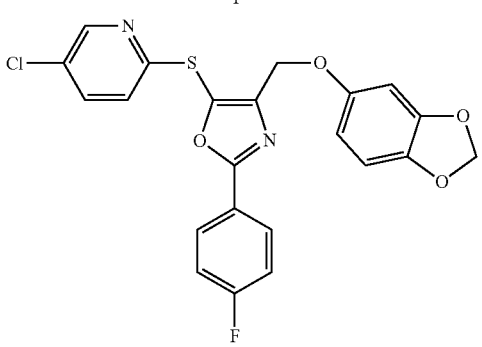
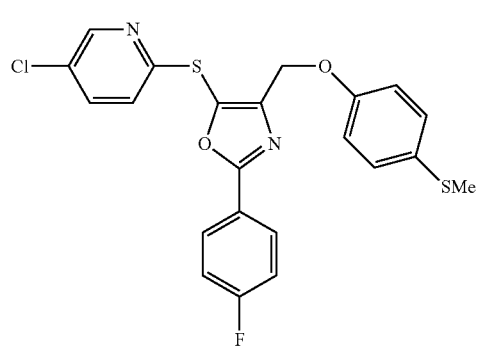
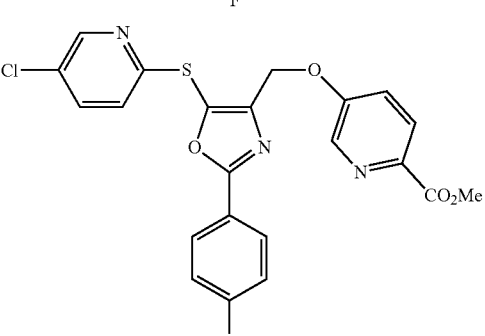
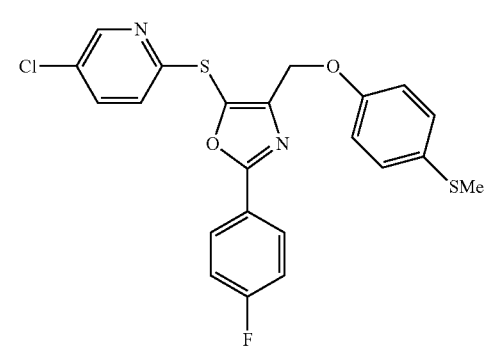
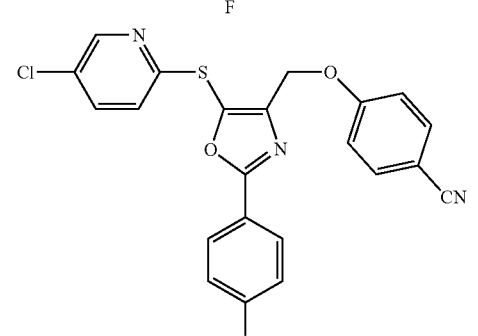
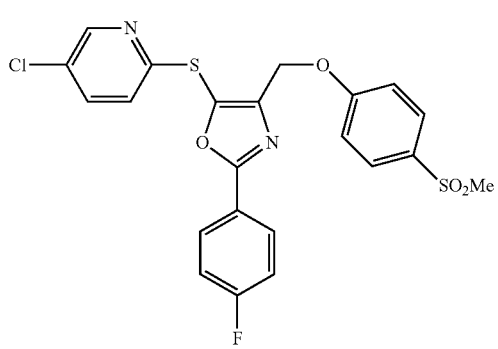
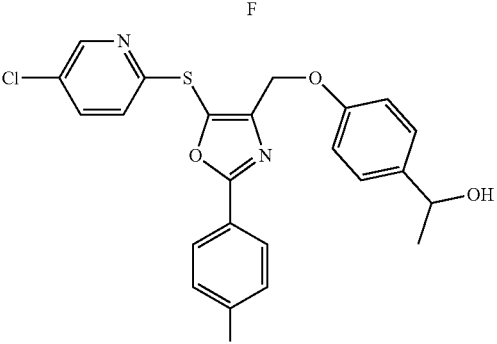

-continued
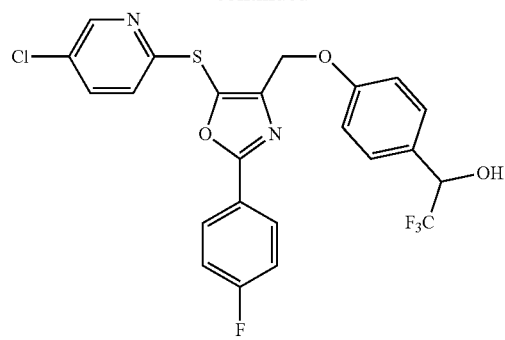
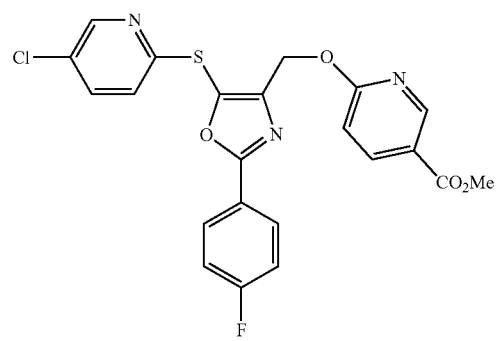
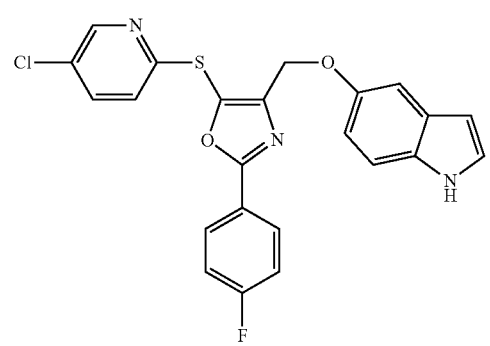 [SMILES: Fc1ccc(-c2nc(COc3ccc4[nH]ccc4c3)c(Sc3ccc(Cl)cn3)o2)cc1]
or a pharmaceutically acceptable salt thereof.
4. A compound selected from the group consisting of
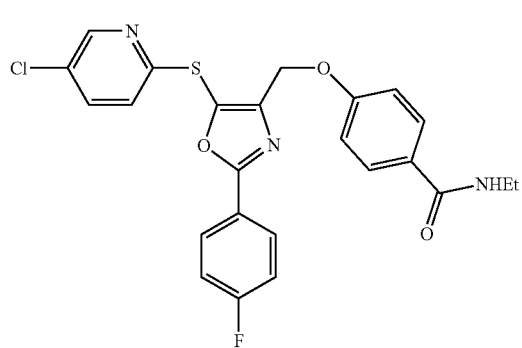
-continued
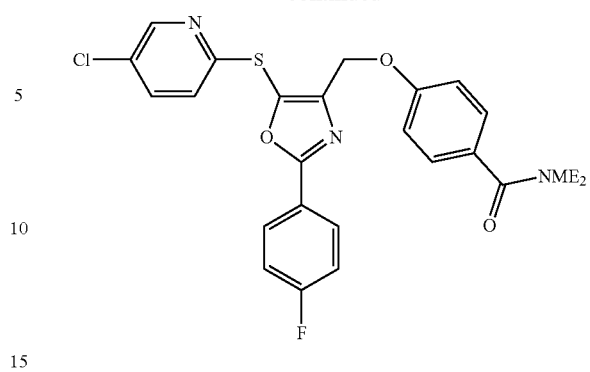
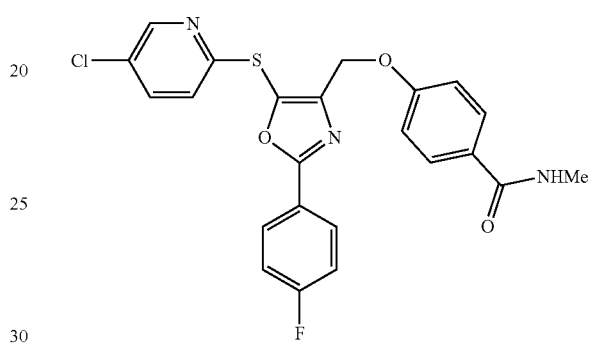
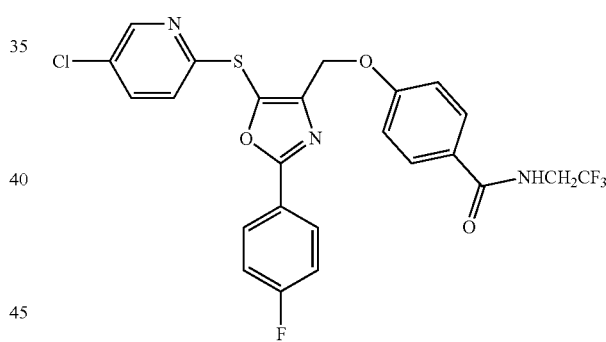
or a pharmaceutically acceptable salt thereof.
5. A compound selected from the group consisting of
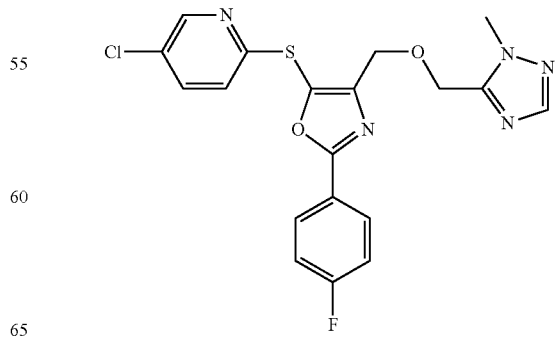

-continued
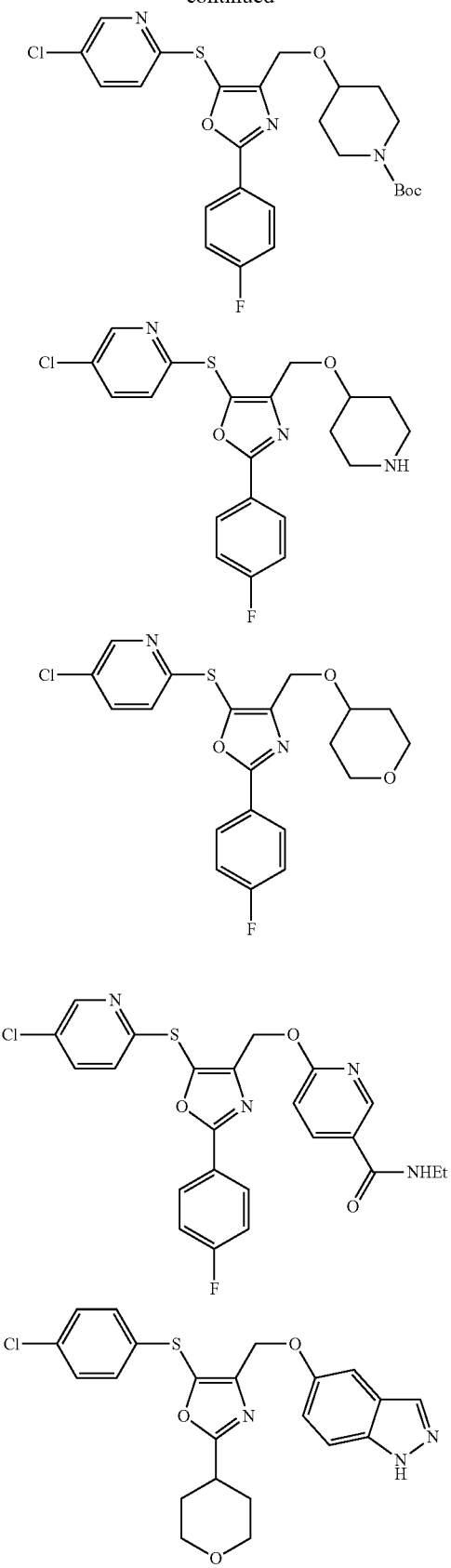
or a pharmaceutically acceptable salt thereof.
6. A compound selected from the group consisting of
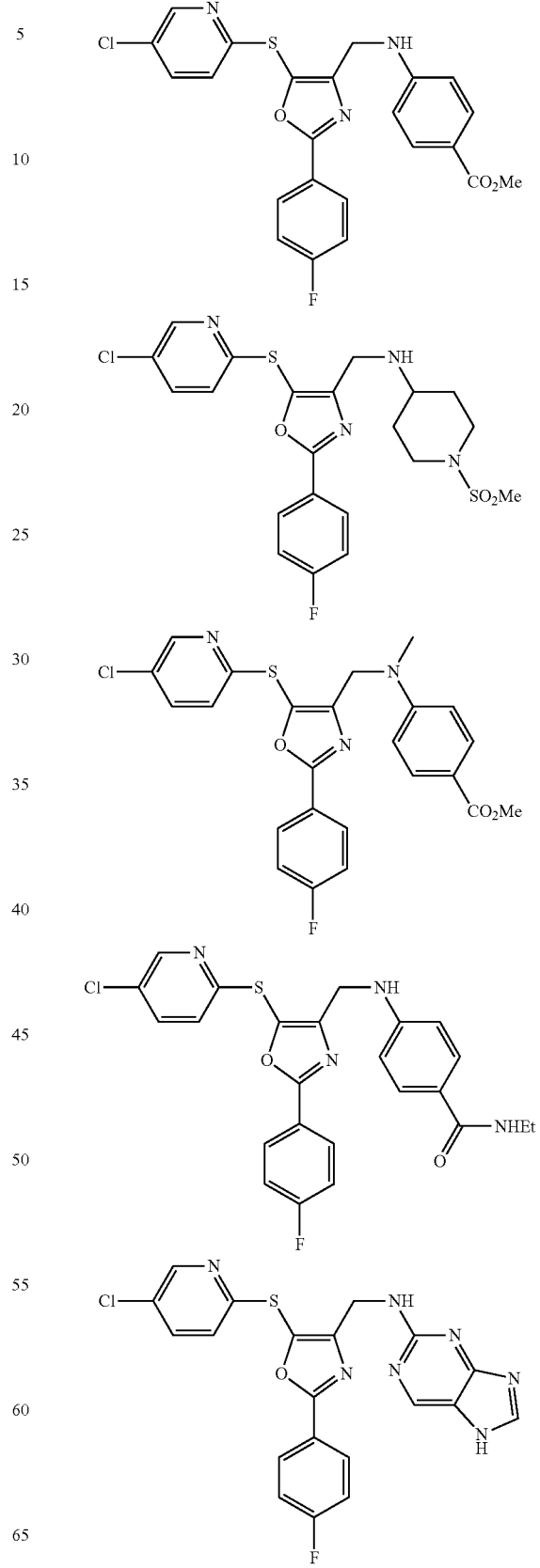

71
-continued
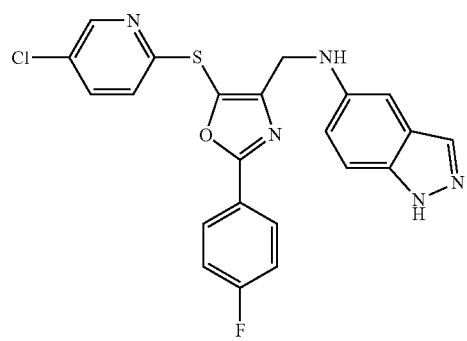
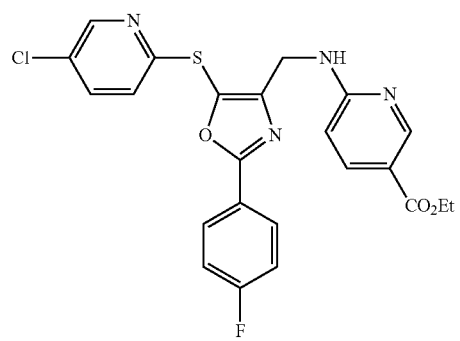
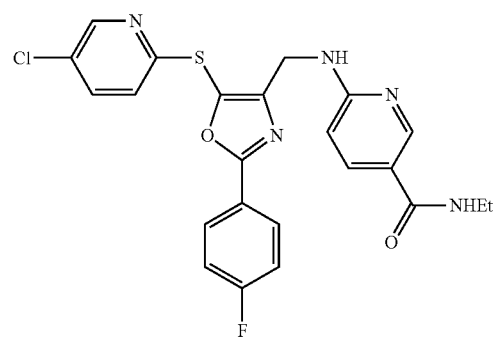
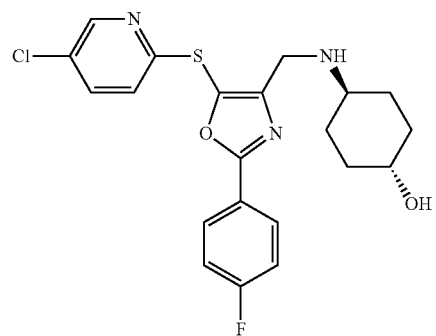
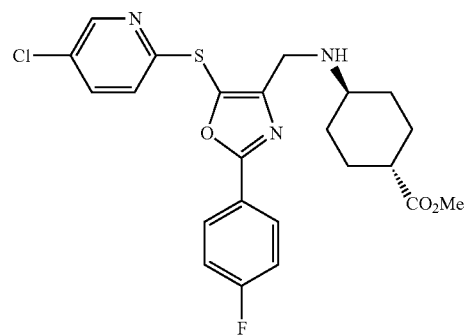
72
-continued
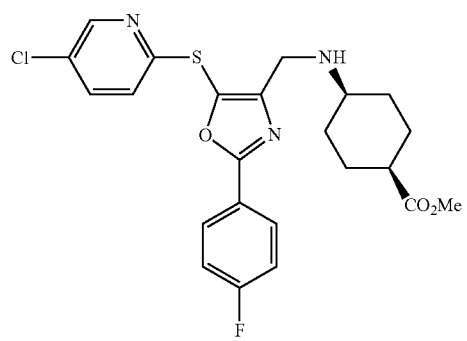
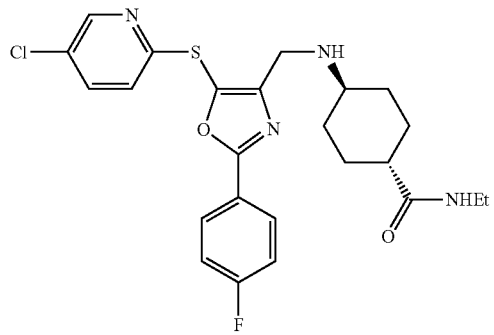
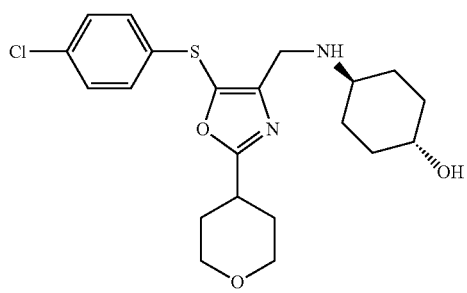
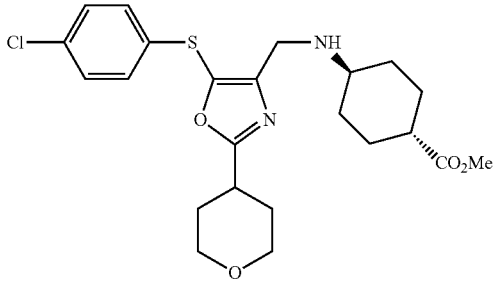
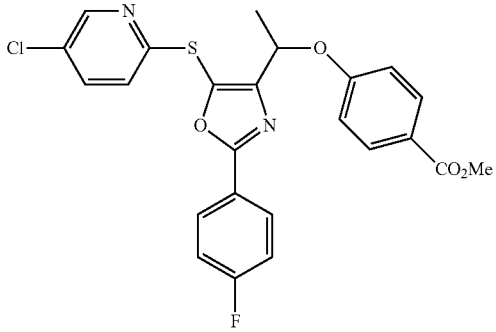

-continued
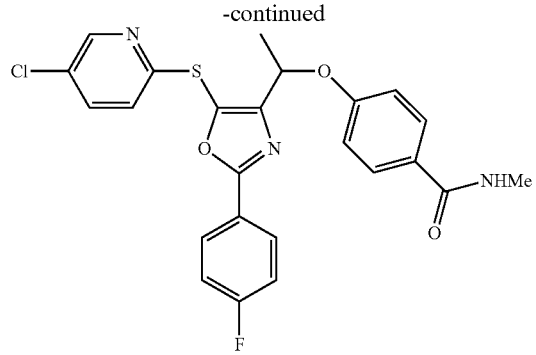
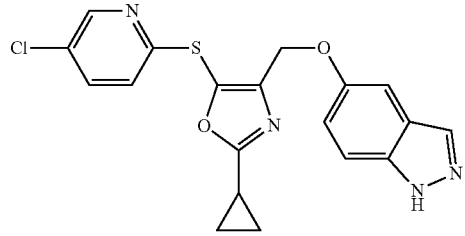
or a pharmaceutically acceptable salt thereof.
7. A pharmaceutical composition which comprises an inert carrier and a compound of claim 1 or a pharmaceutically acceptable salt thereof.
* * * * *